United States Patent

Büttelmann et al.

Patent Number: 5,885,986
Date of Patent: Mar. 23, 1999

[54] OXAZOLYL- AND THIAZOLYLIMIDAZO-BENZO- AND THIENODIAZEPINES AND THEIR USE AS MEDICAMENTS

[75] Inventors: Bernd Büttelmann, Schopfheim, Germany; Thierry Godel, Basel, Switzerland

[73] Assignee: Hoffmann-La Roche Inc., Nutley, N.J.

[21] Appl. No.: 817,665

[22] PCT Filed: Nov. 8, 1995

[86] PCT No.: PCT/EP95/04393

§ 371 Date: Apr. 22, 1997

§ 102(e) Date: Apr. 22, 1997

[87] PCT Pub. No.: WO96/15129

PCT Pub. Date: May 23, 1996

[30] Foreign Application Priority Data

Nov. 11, 1994 [CH] Switzerland ............... 3386/94
Aug. 4, 1995 [CH] Switzerland ............... 2261/95

[51] Int. Cl.⁶ ............... C07D 487/04; C07D 487/14; C07D 495/14; A61K 31/55
[52] U.S. Cl. ............... 514/220; 544/494; 544/498
[58] Field of Search ............... 514/220; 540/498, 540/494

[56] References Cited

U.S. PATENT DOCUMENTS

| | | | |
|---|---|---|---|
| 4,316,839 | 2/1982 | Gerecke et al. | 424/273 |
| 4,771,051 | 9/1988 | Watjen et al. | 514/267 |
| 4,775,671 | 10/1988 | Hunkeler et al. | 514/220 |
| 5,387,585 | 2/1995 | Borer et al. | 514/219 |
| 5,665,718 | 9/1997 | Godel | 514/220 |

FOREIGN PATENT DOCUMENTS

| | | |
|---|---|---|
| 0 027 214 | 4/1981 | European Pat. Off. |
| 0 150 040 | 7/1985 | European Pat. Off. |
| 0 197 282 | 10/1986 | European Pat. Off. |
| 0 519 307 | 12/1992 | European Pat. Off. |

OTHER PUBLICATIONS

Heterocycles vol. 39, No. 2, Dec. 31, 1994 pp. 693–720 Gereck et al (1994).
Nature 294, pp. 763–765 (1981) Mohler et al.
J. Neurochemistry 37, pp. 714–722 (1981) Mohler.

*Primary Examiner*—Mark L. Berch
*Attorney, Agent, or Firm*—George W. Johnston; Dennis P. Tramaloni

[57] ABSTRACT

The invention is concerned with basically-substituted imidazodiazepinones of the formula:

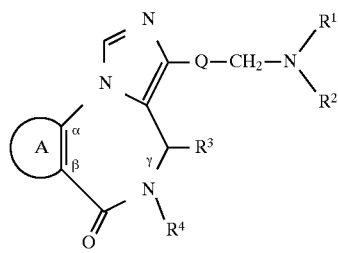

wherein A and the two carbon atoms denoted by $\alpha$ and $\beta$ together signify:

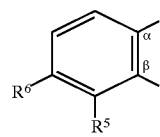

(A¹)

Q signifies one of the residues:

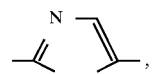

(Q¹)

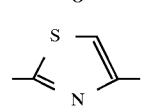

(Q²)

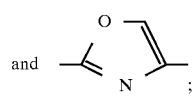

(Q³)

$R^1$ and $R^2$ each signify hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl or together with the nitrogen atom signify a 5- to 8-membered heterocycle optionally containing a further hetero atom or a fused benzene ring; $R^3$ signifies hydrogen and $R^4$ signifies lower alkyl or $R^3$ and $R^4$ together signify a di- or trimethylene group and; $R^5$ and $R^6$ each signify hydrogen, halogen, trifluoromethyl, lower alkoxy or nitro; with the carbon atom denoted by $\gamma$ having the S-configuration when $R^3$ is different from hydrogen, and pharmaceutically acceptable acid addition salts thereof. These compounds can be used as anxiolytic and/or anticonvulsant and/or muscle relaxant and/or sedative-hypnotic active substances.

16 Claims, No Drawings

OXAZOLYL- AND THIAZOLYLIMIDAZO-BENZO- AND THIENODIAZEPINES AND THEIR USE AS MEDICAMENTS

This application is a 371 of PCT/EP95/04393, filed Nov. 08, 1995.

The present invention is concerned with imidazodiazepinones of the general formula

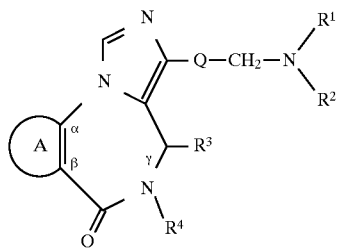

wherein A and the two carbon atoms denoted by α and β together signify one of the residues

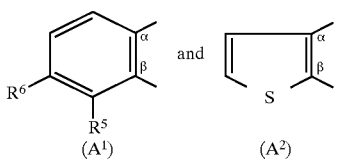

Q signifies one of the residues

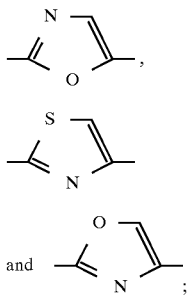

$R^1$ and $R^2$ each signify hydrogen, lower alkyl, lower alkenyl, lower alkynyl, lower hydroxyalkyl, lower alkoxy-lower alkyl, $(C_3-C_6)$-cycloalkyl, $(C_3-C_6)$-cycloalkyl-lower alkyl, amino-lower alkyl, lower alkylamino-lower alkyl, di-lower alkylamino-lower alkyl or aryl-lower alkyl or together with the nitrogen atom signify a 5- to 8-membered heterocycle optionally containing a further hetero atom or a fused benzene ring, $R^3$ signifies hydrogen and $R^4$ signifies lower alkyl or $R^3$ and $R^4$ together signify a di- or trimethylene group and $R^5$ and $R^6$ each signify hydrogen, halogen, trifluoromethyl, lower alkoxy or nitro, with the carbon atom denoted by γ having the S-configuration when $R^3$ is different from hydrogen, and pharmaceutically acceptable acid addition salts thereof.

These compounds are novel and have valuable pharmacodynamic properties. They are therefore suitable for therapeutic purposes, especially for anxiolytic and/or anticonvulsant and/or muscle relaxant and/or sedative-hypnotic purposes.

Objects of the present invention are the mentioned compounds of formula I and salts thereof per se and as therapeutically active substances, their manufacture and their use for therapeutic purposes or for the production of corresponding medicaments as well as medicaments containing a compound of formula I or a salt thereof and the production of such medicaments.

The term "lower" denotes residues or compounds with a maximum of 7, preferably a maximum of 4, carbon atoms. The term "alkyl" denotes straight-chain or branched saturated hydrocarbon residues such as methyl, ethyl, n-propyl, iso-propyl, n-butyl, sec.-butyl, isobutyl and tert.-butyl. The term "alkoxy" denotes alkyl groups bonded via an oxygen atom, such as methoxy and ethoxy. The term "cycloalkyl" denotes saturated cyclic hydrocarbon residues such as e.g. cyclopropyl. The terms "alkenyl" and "alkynyl" denote straight-chain or branched hydrocarbon residues which contain a C—C double or, respectively, triple bond, such as allyl, but-2-enyl, 3-methyl-but-2-enyl, propargyl and the like. The term "aryl" denotes a phenyl residue optionally substituted by halogen, trifluoromethyl, lower alkyl or lower alkoxy. The term "halogen" embraces fluorine, chlorine, bromine and iodine. When $R^3$ signifies hydrogen and $R^4$ signifies lower alkyl or $R^3$ and $R^4$ together signify a di- or trimethylene group and $R^5$ and $R^6$ each signify hydrogen, halogen, trifluoromethyl, lower alkoxy or nitro, with the carbon atom denoted by g having the S-configuration when $R^3$ is different from hydrogen, and pharmaceutically acceptable acid addition salts thereof.

European Patent Application EP-A-197282 relates to oxadiazolyl imidazobenzodiazepine derivatives and to methods for preparing such compounds. These compounds are suitable for use in psychopharmaceutical preparations as anticonvulsants, anxiolytics, hypnotics and nootropics. European Patent Application EP-A-519307 refers to tetracyclic imidazodiazepines useful for the prevention of epilepsy, anxiety, and related diseases. The compounds of the present invention are novel and have improved pharmacodynamic properties. They are therefore suitable for therapeutic purposes, especially for anxiolytic and/or anticonvulsant and/or muscle relaxant and/or sedative-hypnotic purposes.

Objects of the present invention are the mentioned compounds of formula I and salts thereof per se and as therapeutically active substances, their manufacture and their use for therapeutic purposes or for the production of corresponding medicaments as well as medicaments containing a compound of formula I or a salt thereof and the production of such medicaments.

The term "lower" denotes residues or compounds with a maximum of 7, preferably a maximum of 4, carbon atoms. The term "alkyl" denotes straight-chain or branched saturated hydrocarbon residues such as methyl, ethyl, n-propyl, iso-propyl, n-butyl, sec.-butyl, isobutyl and tert.-butyl. The term "alkoxy" denotes alkyl groups bonded via an oxygen atom, such as methoxy and ethoxy. The term "cycloalkyl" denotes saturated cyclic hydrocarbon residues such as e.g. cyclopropyl. The terms "alkenyl" and "alkynyl" denote straight-chain or branched hydrocarbon residues which contain a C—C double or, respectively, triple bond, such as allyl, but-2-enyl, 3-methyl-but-2-enyl, propargyl and the like. The term "aryl" denotes a phenyl residue optionally substituted by halogen, trifluoromethyl, lower alkyl or lower alkoxy. The term "halogen" embraces fluorine, chlorine, bromine and iodine. When $R^1$ and $R^2$ together with the nitrogen atom signify a heterocycle, then this is a residue such as 1-pyrrolidinyl, piperidino, morpholino, 4-methyl-1-piperazinyl, isoindolin-2-yl and the like.

3

When Q in formula I signifies a residue of formula $Q^1$, there are especially preferred compounds in which $R^1$ and $R^2$ each signify lower alkyl, A signifies a residue of formula $A^1$ in which $R^5$ and $R^6$ each signify hydrogen or halogen or a residue $A^2$ in which $R^3$ signifies hydrogen and $R^4$ signifies methyl or $R^3$ and $R^4$ together signify a di- or trimethylene group.

Especially preferred compounds of formula I are:

3-(5-Dipropylaminomethyl-oxazol-2-yl)-8-fluoro-5-methyl-5,6-dihydro-4H-imidazo[1,5-a][1,4]benzodiazepin-6-one;

(S)-1-(5-dipropylaminomethyl-oxazol-2-yl)-11,11a-dihydro-8H,10H-azeto[1,2-a]imidazo[5,1-c]thieno[3,2-a][1,4]-diazepin-8-one;

(S)-8-chloro-1-(5-dipropylaminomethyl-oxazol-2-yl)-12,12a-dihydro-9H,11H-azeto[2,1-c]imidazo[1,5-a][1,4]benzodiazepin-9-one;

7-chloro-3-(5-dipropylaminomethyl-oxazol-2-yl)-8-fluoro-5-methyl-5,6-dihydro-4H-imidazo[1,5-a][1,4]benzodiazepin-6-one;

3-(5-dipropylaminomethyl-oxazol-2-yl)-5-methyl-5,6-dihydro-4H-imidazo[1,5-a][1,4]benzodiazepin-6-one;

7-chloro-3-(5-dipropylaminomethyl-oxazol-2-yl)-5-methyl-5,6-dihydro-4H-imidazo[1,5-a][1,4]benzodiazepin-6-one;

3-(5-dibutylaminomethyl-oxazol-2-yl)-8-fluoro-5-methyl-5,6-dihydro-4H-imidazo[1,5-a][1,4]benzodiazepin-6-one and 3-(5-dipropylaminomethyl-oxazol-2-yl)-5-methyl-5,6-dihydro-4H-imidazo[1,5-a]thieno[2,3-f][1,4]diazepin-6-one.

When Q in formula I signifies a residue of formula $Q^2$, there are especially preferred compounds in which $R^1$ and $R^2$ each signify lower alkyl, A signifies a residue of formula $A^1$, $R^3$ signifies hydrogen and $R^4$ signifies methyl or $R^3$ and $R^4$ together signify a di- or trimethylene residue.

These include, for example, the following compounds:

7-Chloro-3-(4-dipropylaminomethyl-thiazol-2-yl)-5-methyl-5,6-dihydro-4H-imidazo[1,5-a][1,4]benzodiazepin-6-one;

(S)-8-chloro-1-(4-dipropylaminomethyl-thiazol-2-yl)-12,12a-dihydro-9H,11H-azeto[2,1-c]amidazo[1,5-a][1,4]benzodiazepin-9-one;

(S)-8-chloro-1-(4-dipropylaminomethyl-thiazol-2-yl)-11,12,13,13a-tetrahydro-9H-imidazo[1,5-a]pyrrolo[2,1-c][1,4]-benzodiazepin-9-one and 7-chloro-3-(4-dipropylaminomethyl-thiazol-2-yl)-8-fluoro-5-methyl-5,6-dihydro-4H-imidazo[1,5-a][1,4]benzodiazepin-6-one.

When Q in formula I signifies a residue of formula $Q^3$, there are especially preferred compounds in which $R^1$ and $R^2$ each signify lower alkyl, A signifies a residue of formula $A^1$, $R^3$ signifies hydrogen and $R^4$ signifies methyl.

These include, for example, the following compound:

7-Chloro-3-(4-dipropylaminomethyl-oxazol-2-yl)-5-methyl-5,6-dihydro-4H-imidazo[1,5-a][1,4]benzodiazepin-6-one.

The compounds of formula I mentioned earlier and their pharmaceutically acceptable acid addition salts can be manufactured in accordance with the invention by

4 a) reacting a compound of the general formula

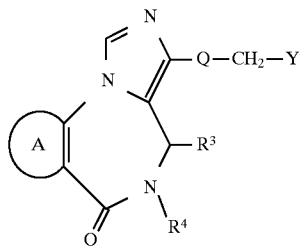

II wherein A, Q, $R^3$ and $R^4$ have the above significance and Y signifies a leaving group, with an amine of the general formula

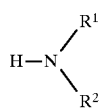

III wherein $R^1$ and $R^2$ have the above significance, or b) cleaving off the protecting group(s) from a compound of the general formula

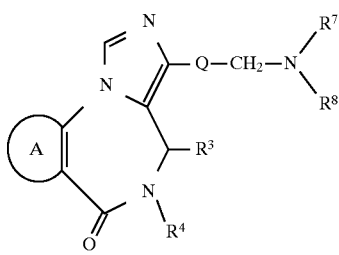

IV wherein A, Q, $R^3$ and $R^4$ have the above significance and $R^7$ signifies a protecting group, protected lower hydroxyalkyl, protected amino-lower alkyl or protected lower alkyl-amino-lower alkyl and $R^8$ signifies hydrogen, lower alkyl, lower alkenyl, lower alkynyl, protected lower hydroxyalkyl, lower alkoxy-lower alkyl, ($C_3$–$C_6$)-cycloalkyl, ($C_3$–$C_6$)-cycloalkyl-lower alkyl, protected amino-lower alkyl, protected lower alkylamino-lower alkyl, di-lower alkyl-amino-lower alkyl, or aryl-lower alkyl or $R^7$ and $R^8$ together signify a protecting group, or c) appropriately N-alkylating a compound of the general formula

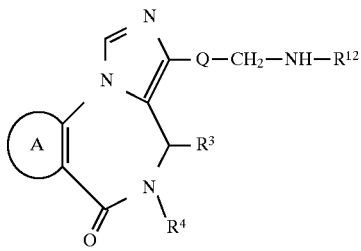

Ia wherein A, Q, $R^3$ and $R^4$ have the above significance and $R^{12}$ signifies hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkyl-amino-lower alkyl or aryl-lower alkyl, or d) reducing a compound of the general formula

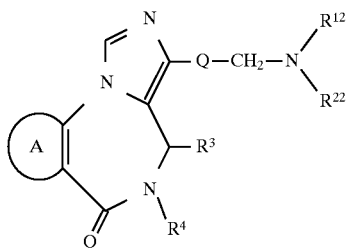

wherein A, Q, $R^3$ and $R^4$ and $R^{12}$ have the above significance and $R^{22}$ signifies lower alkenyl or lower alkynyl, and, if desired, e) converting a compound of general formula I into a pharmaceutically usable acid addition salt.

Compounds of formula I in which $R^1$ and $R^2$ have the significance mentioned earlier are obtained according to process variant a). The leaving group denoted by Y in formula II is conveniently a halogen atom, preferably an iodine or chlorine atom. The reaction of a compound of formula II with an amine of formula III is effected in the presence of an inert solvent such as N,N-dimethylformamide and in the presence of a base, conveniently an organic base, e.g. a tertiary amine such as N-ethyldiisopropylamine or the like, whereby an excess of the amine of formula III can also serve as the organic base.

The following are especially suitable as the amine of formula III: dipropylamine, diallylmine, diethylamine, propylamine, diisopropylamine, dibutylamine, piperidine, dimethylamine, pyrrolidine and the like.

Compounds of formula I in which R signifies hydrogen, lower hydroxyalkyl, amino-lower alkyl or lower alkylamino-lower alkyl and $R^2$ signifies hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl are obtained in accordance with process variant b). Suitable protecting groups and methods for their cleavage will be familiar to any person skilled in the art, although of course there can be used only those protecting groups which can be cleaved off by methods under the conditions of which other structural elements in the compounds of formula IV are not affected.

The tert.-butoxycarbonyl group (BOC), which can be cleaved off by means of trifluoroacetic acid, is, for example, a suitable N-protecting group.

The tert.-butyl group (tBu), which can also be cleaved off by means of trifluoroacetic acid, is, for example, a suitable O-protecting group.

Compounds of formula I in which at least one of $R^1$ and $R^2$ is different from hydrogen are obtained in accordance with process variant c). Suitable alkylating agents and alkylating methods will be familiar to any person skilled in the art. Particularly suitable alkylating agents are corresponding halides such as propyl bromide, propyl iodide, butyl iodide, allyl bromide, crotyl bromide, 4-bromo-1-butene, 3,3-dimethylallyl bromide, propargyl bromide, cyclopropylmethyl bromide, benzyl bromide or α,α'-dibromo-o-xylene (whereby by means of the latter a $NH_2$ group can be converted into an isoindolin-2-yl group). The alkylation is effected in the presence of a base, conveniently an organic base such as N-ethyldiisopropylamine, 1,8-diazabicyclo[5.4.0]undec-7-ene (1,5-5) or the like. Furthermore, the alkylation is conveniently effected in an inert solvent such as N,N-dimethylformamide.

Compounds of formula I in which at least one of $R^1$ and $R^2$ signifies lower alkyl are obtained in accordance with process variant d) from corresponding compounds of formula I in which at least one of $R^1$ and $R^2$ signifies lower alkenyl or lower alkynyl, i.e. from compounds of formula Ib, by reduction of the C—C double or triple bond. This reduction is conveniently effected by catalytic hydrogenation, for example in the presence of a palladium catalyst such as Pd/C. Furthermore, this reduction is effected in an inert solvent such as ethyl acetate.

The compounds of formula I can be converted into pharmaceutically acceptable acid addition salts in accordance with process variant e). Not only salts with inorganic acids, but also salts with organic acids come into consideration. Examples of such salts are the hydrochlorides, hydrobromides, sulphates, nitrates, citrates, acetates, maleates, succinates, methanesulphonates, p-toluenesulphonates and the like. These salts can be manufactured according to methods which are known per se and which will be familiar to any person skilled in the art.

The starting materials of formulae IIa, IIb and IIc can be prepared according to Schemes 1 and 2 hereinafter:

Scheme 1

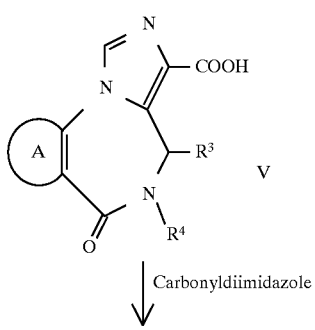

Carbonyldiimidazole

-continued
Scheme 1
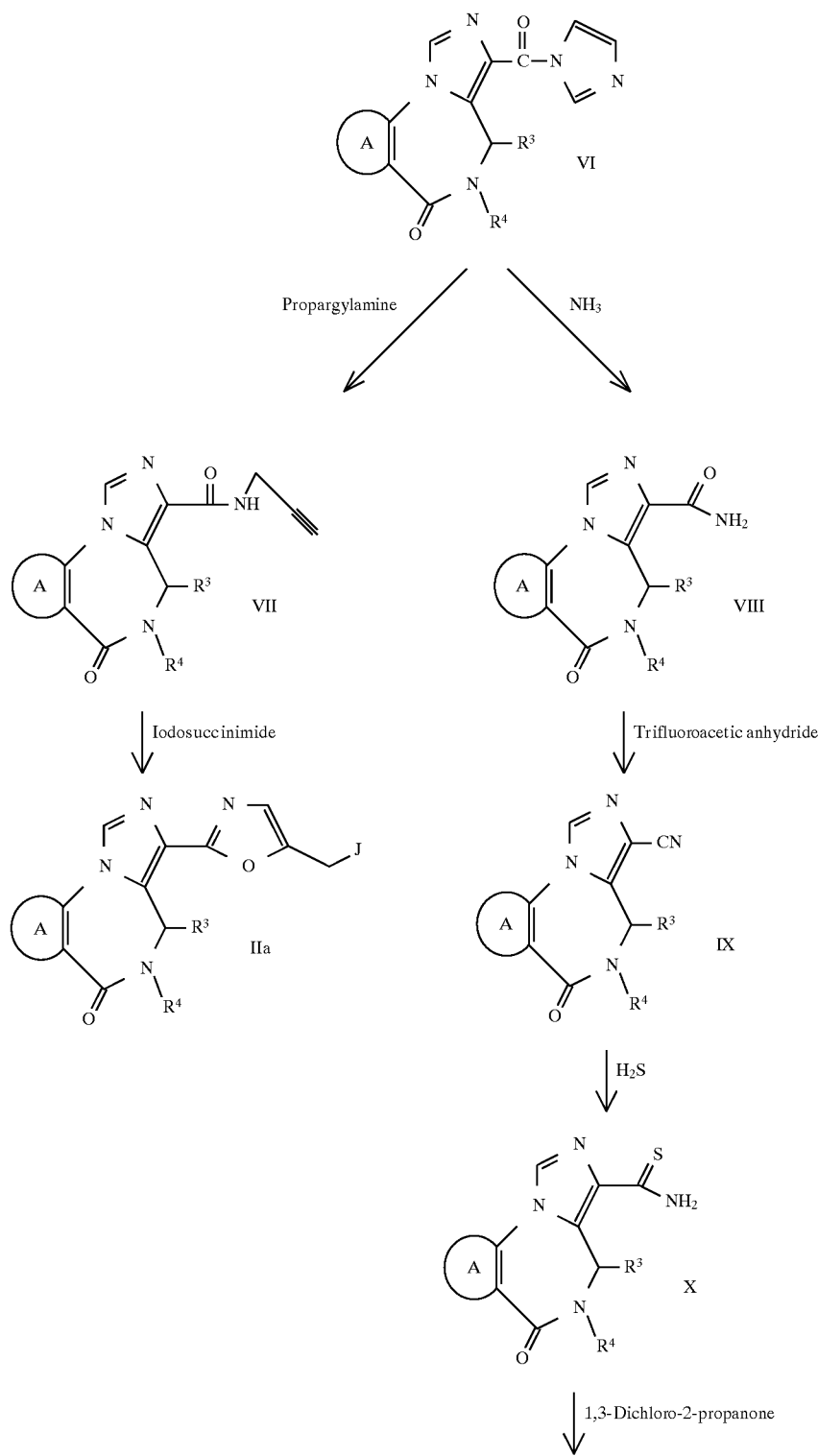

-continued
Scheme 1

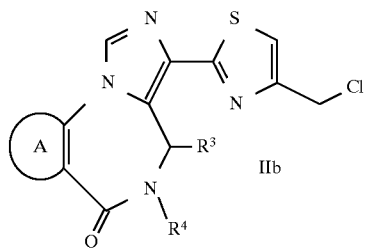

A and R¹–R⁴ have the singificance set forth earlier

Scheme 2

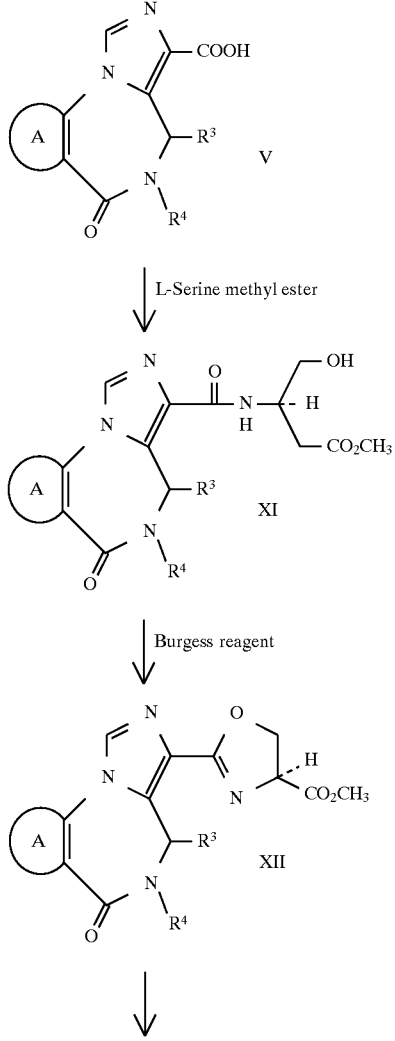

-continued
Scheme 2

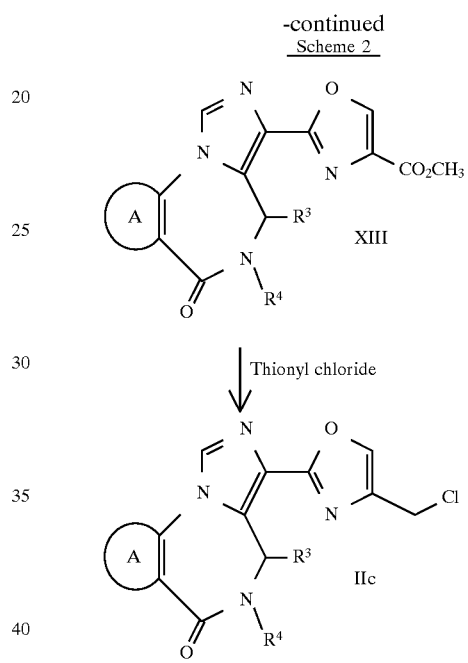

A und R¹–R⁴ have the significances set forth earlier

The starting materials are conveniently prepared from compounds of formula V, which are known compounds (see EP 0 150 040 A2 and EP 0 027 214 A1).

The following procedure can be used:

Conveniently, a compound of formula V is reacted with carbonyldiimidazole under a protective gas atmosphere in an inert solvent, for example N,N-dimethylformamide. After completion of the reaction, i.e. after completion of the $CO_2$ evolution, and subsequent stirring for several hours the compound of general formula VI can be converted without isolation either into compounds of general formula IIa or IIb.

A compound of formula IIa is obtained by reacting this solution obtained with propargylamine and subsequently with iodosuccinimide. A detailed description of this process variant follows in Examples 1–17.

A compound of general formula IIb is obtained via several process steps as follows: The solution containing a compound of formula VI is conveniently firstly treated with a NH₃ stream, whereby compounds of general formula VIII result. After working up these are reacted with trifluoroacetic anhydride in the presence of dioxan and pyridine to give compounds of general formula IX, with the reaction temperature lying at about 0° C.

Subsequently, a hydrogen sulphide stream is conducted through the resulting compound IX dissolved in pyridine and triethylamine. Conveniently, this solution is subsequently left to stand for several hours and then de-gassed in a nitrogen stream. The thus-obtained compound of general formula X can subsequently be converted with 1,3-dichloro-2-propanone into the compound of formula IIb.

A detailed description of the process steps follows in Examples 18–27.

A detailed description of the preparation of the compounds of formula IIc according to Scheme 2 follows in Examples 28–31.

The amines of general formula III (process variant a)) are commercial products or can be prepared according to methods which will be familiar to any person skilled in the art.

Compounds of general formula IV are obtained by the selective introduction of protecting groups into corresponding compounds of general formula I using conventional protecting group reagents. These methods will also be familiar to a person skilled in the art.

As mentioned earlier, the compounds of formula I are novel. They have valuable pharmacodynamic properties and exhibit only a low toxicity. They have as a common feature a pronounced affinity to the central benzodiazepine receptors and, because of their agonistic activity at these receptors, they have pronounced anxiolytic, anticonvulsant, muscle relaxant and sedative-hypnotic properties. They form acid addition salts which have very good water solubility and are therefore primarily suitable for the production of aqueous injection solutions.

The affinity of compounds of general formula I to the central benzodiazepine receptors has been established in vitro according to the methods described in Nature 294, 763–765 (1981) and J. Neurochemistry 37, 714–722 (1981). According to these methods, the inhibition of the binding of tritiated flumazenil to the specific benzodiazepine receptors in the cortex of rats by the respective test substances is determined. The $IC_{50}$ ("50% inhibiting concentration") denotes that concentration of the respective test substance which brings about a 50 percent inhibition of the specific binding of tritiated flumazenil to the specific benzodiazepine receptors in the cortex of rats.

The sedative/muscle relaxant properties of the compounds of formula I in accordance with the invention can be determined, for example, in the rotating rod test. Mice weighing 19–21 g are used for this test. They have free access to feed and drinking water up to 1 h before the beginning of the test. They are brought into the test laboratory at least 30 min. before the test. In the rotating rod test the animals are placed on a horizontally arranged, smooth metal rod having a diameter of 3 cm, which is rotated at 2 revolutions per min. Initially, the animals are given the opportunity of familiarizing themselves with the test situation for 30 sec. Subsequently, those animals which succeed in remaining on the rod for at least 1 min. are selected. These animals are then given the test preparations intravenously in different dosages. At various points in time it is then determined whether the animals are able to remain on the rod for a minimum period (minimum period: 10 sec.; from 5 min. after administration: 1 min.). That dosage at which 50% of the animals are capable of remaining on the rod ($ED_{50}$) is determined.

The results which have been obtained with representative members of the class of compound defined by general formula I in the tests described previously are compiled in the following Table.

TABLE

| Compound | Affinity to benzodiazepine receptors $IC_{50}$, [nM] | Rotating rod test, $ED_{50}$ in mg/kg, i.v., determined at the following points in time after administration | | | | | | | |
|---|---|---|---|---|---|---|---|---|---|
| | | 15 sec | 30 sec | 60 sec | 2 min | 5 min | 15 min | 30 min | 60 min |
| A | 32 | 0.3 | 0.4 | 0.6 | 1.1 | 1.8 | >10 | >10 | >10 |
| B | 59 | 0.3 | 0.5 | 0.7 | 1.6 | 2.6 | 4.9 | >10 | >10 |
| C | 7.0 | 0.3 | 0.3 | 0.5 | 0.7 | 1.6 | 2.0 | >10 | ≧10 |
| D | 7 | 0.1 | 0.2 | 0.4 | 0.5 | 1.8 | 3.6 | >10 | >10 |
| E | 11 | 0.3 | 0.3 | 0.3 | 0.9 | 1.0 | 3.2 | ≧10 | >10 |
| F | 66 | 1.7 | 3,9 | 4.7 | ≧10 | ≧10 | >10 | >10 | >10 |
| G | 4 | 1.0 | 1.2 | 1.8 | 2.1 | 3.0 | 3.4 | 5.6 | >10 |
| H | 35 | 1.1 | 1.1 | 1.2 | 2.1 | 3.4 | ≧10 | >10 | >10 |
| I | 17 | 1.8 | 1.7 | 3.4 | 3.9 | 8.7 | >10 | >10 | >10 |
| J | 5.2 | 0.7 | 0.9 | 2.3 | ≧10 | ≧10 | >10 | >10 | >10 |
| K | 15 | 1.8 | 1.8 | 5.6 | 3.7 | 5.6 | ≧10 | ≧10 | >10 |
| L | 16 | 1.1 | 1.1 | 1.1 | 2.8 | 4.7 | 5.7 | ≧10 | >10 |
| M | 15 | 0.4 | 1.0 | 1.2 | 3.0 | 3.7 | 8.8 | ≧10 | >10 |

A: (S)-8-Chloro-1-(5-dipropylaminomethyl-oxazol-2-yl)-12,12a-dihydro-9H,11H-azeto[2,1-c]imidazo[1,5-a][1,4]benzo-diazepin-9-one.
B: 3-(5-Dipropylaminomethyl-oxazol-2-yl)-8-fluoro-5-methyl-5,6-dihydro-4H-imidazol[1,5-a][1,4]benzodiazepin-6-one.
C: 7-Chloro-3-(5-dipropylaminomethyl-oxazol-2-yl)-8-fluoro-5-methyl-5,6-dihydro-4H-imidazo[1,5-a][1,4]benzodiazepin-6-one.
D: (S)-1-(5-Dipropylaminomethyl-oxazol-2-yl)-11,11a-dihydro-8H,10H-azeto[1,2-a]imidazo[5,1-c]thieno[3,2-e][1,4]diazepin-8-one.
E: (S)-8-Chloro-1-(4-dipropylaminomethyl-thiazol-2-yl)-12,12a-dihydro-9H,11H-azeto[2,1-c]imidazo[1,5-a][1,4]-benzodiazepin-9-one.
F: 3-(5-Dipropylaminomethyl-oxazol-2-yl)-5-methyl-5,6-dihydro-4H-imidazo[1,5-a][1,4]benzodiazepin-6-one.
G: 7-Chloro-3-(5-dipropylaminomethyl-oxazol-2-yl)-5-methyl-5,6-dihydro-4H-imidazo[1,5-a][1,4]benzodiazepin-6-one.
H: 3-(5-Dibutylaminomethyl-oxazol-2-yl)-8-fluoro-5-methyl-5,6-dihydro-4H-imidazol[1,5-a][1,4]benzodiazepin-6-one.
I: 3-(5-Dipropylaminomethyl-oxazol-2-yl)-5-methyl-5,6-dihydro-4H-imidazo[1,5-a]thieno[2,3-f][1,4]diazepin-6-one.
J: 7-Chloro-3-(4-dipropylaminomethyl-thiazol-2-yl)-5-methyl-5,6-dihydro-4H-imidazo[1,5-a][1,4]benzodiazepin-6-one.
K: (S)-8-Chloro-1-(4-dipropylaminomethyl-thiazol-2-yl)-11,12,13,13a-tetrahydro-9H-imidazo[1,5-a]pyrrolo[2,1-c][1,4]benzodiazepin-9-one.
L: 7-Chloro-3-(4-dipropylaminomethyl-thiazol-2-yl)-8-fluoro-5-methyl-5,6-dihydro-4H-imidazo[1,5-a][1,4]benzodiazepin-6-one.
M: 7-Chloro-3-(4-dipropylaminomethyl-oxazol-2-yl-5-methyl-5,6-dihydro-4H-imidazo[1,5-a][1,4]benzodiazepin-6-one.

From the above Table it will be evident that compounds A to M display a sedative activity which sets in very rapidly and which lasts only a relatively short time.

Having regard to their agonistic activity on the benzodiazepine receptors, the compounds of formula I can be used as sedatives/hypnotics, anticonvulsants, muscle relaxants and anxiolytics. They are suitable, for example, as rapid, but short acting hypnotics for peroral administration, but especially—in the form of aqueous solutions of their acid addition salts—as injectable short-term hypnotics for premedication, sedation as well as narcosis induction and narcosis maintenance; preferred possible applications are thus premedication prior to narcosis induction, basal sedation prior to diagnostic or surgical intervention with or without local anaesthesia, long-term sedation in intensive care nursing wards, use as an induction agent in inhalation narcosis or as a sleep-inducing component in combination narcosis (including total intravenous anaesthesia) etc.

The compounds of formula I and pharmaceutically acceptable acid addition salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and pharmaceutically acceptable acid addition salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Adjuvants such as alcohols, polyols, glycerol, vegetable oils and the like can be used for aqueous injection solutions of water-soluble acid addition salts of compounds of formula I, but as a rule are not necessary. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

As mentioned earlier, medicaments containing a compound of formula I or a pharmaceutically acceptable acid addition salt thereof and a therapeutically inert excipient are also an object of the present invention, as is a process for the production of such medicaments which comprises bringing one or more compounds of formula I or pharmaceutically acceptable acid addition salts thereof and, if desired, one or more other therapeutically valuable substances into a galenical administration form together with one or more therapeutically inert carriers.

As mentioned earlier, the compounds of formula I and pharmaceutically acceptable acid addition salts thereof can be used in accordance with the invention for therapeutic purposes, especially for anxiolytic and/or anticonvulsant and/or muscle relaxant and/or sedative-hypnotic purposes. The dosage can vary within wide limits and will, of course, be fitted to the individual requirements in each particular case. In general, in the case of intravenous administration a daily dosage of about 1 mg to 1000 mg should be appropriate.

Finally, as mentioned earlier, the use of compounds of formula I and of pharmaceutically usable acid addition salts thereof for the production of medicaments, especially of anxiolytic and/or anticonvulsant and/or muscle relaxant and/or sedative-hypnotic medicaments, is also an object of the invention.

The following Examples are intended to illustrate the present invention in more detail, but not to limit its scope in any manner. All temperatures are given in degrees Celsius.

EXAMPLE 1 a) A suspension of 5.0 g (0.0194 mol) of 5-methyl-6-oxo-5,6-dihydro-4H-imidazo[1,5-a][1,4]benzodiazepine-3-carboxylic acid in 50 ml of dimethylformamide was treated portionwise with 3.3 g (0.0204 mol) of carbonyldiimidazole while gassing with argon. After the addition of a further 50 ml of DMF and after completion of the $CO_2$ evolution the yellow solution obtained was stirred at 70° for 1 hr. After cooling to room temperature the mixture was treated dropwise with 1.66 ml (0.026 mol) of propargylamine and stirred at room temperature for 1 hr. The yellow solution was completely freed from the solvents and the crystalline residue was suspended in 150 ml of hot water, cooled to room temperature and filtered off under suction. There were obtained 4.9 g (86%) of 5-methyl-6-oxo-5,6-dihydro-4H-imidazo[1,5-a][1,4]benzodiazepine-3-carboxylic acid prop-2-ynylamide as whitish crystals; m.p. 213°–215°.

b) A solution of 2.94 g (0.010 mol) of 5-methyl-6-oxo-5,6-dihydro-4H-imidazo[1,5-a][1,4]benzodiazepine-3-carboxylic acid prop-2-ynylamide in 60 ml of acetic acid was treated with 3.36 g (0.015 mol) of N-iodosuccinimide while gassing with argon. After stirring at room temperature for 46 hrs. the dark suspension obtained was completely freed from the solvents and dried azeotropically several times with toluene. The dark brown solid residue was dissolved in 100 ml of THF, treated with 13.7 ml (0.10 mol) of dipropylamine and stirred at room temperature for 3 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the orange-brownish product was chromatographed over basic Alox (grade III) with dichloromethane/ethyl acetate 4:1 as the eluent and recrystallized from hot isopropyl ether. There was obtained 1.0 g (25%) of 3-(5-dipropylaminomethyl-oxazol-2-yl)-5-methyl-5,6-dihydro-4H-imidazo[1,5-a][1,4]benzodiazepin-6-one as yellowish crystals; m.p. 133°–135°.

c) 1.0 g (0.00254 mol) of 3-(5-dipropylaminomethyl-oxazol-2-yl)-5-methyl-5,6-dihydro-4H-imidazo[1,5-a][1,4]benzodiazepin-6-one in 50 ml of ethyl acetate was treated with 0.76 ml (0.00279 mol) of 3.7N ethanolic hydrochloric acid. After stirring at 0° for ½ hr. the white suspension was suction filtered. The yellowish crystals were dissolved in hot acetonitrile and recrystallized by the addition of ether. There was obtained 0.95 g (87%) of 3-(5-dipropylaminomethyl-oxazol-2-yl)-5-methyl-5,6-dihydro-4H-imidazo [1,5-a][1,4]benzodiazepin-6-one hydrochloride (1:1) as light beige crystals; m.p. 228°–231° (dec.).

EXAMPLE 2 a) A suspension of 8.14 g (0.0302 mol) of (S)-9-oxo-12,12a-dihydro-9H,11H-azeto[2,1-c]imidazo[1,5-a][1,4]benzodiazepine-1-carboxylic acid in 60 ml of dimethylformamide was treated portionwise with 5.14 g (0.0317 mol) of carbonyldiimidazole while gassing with argon. After completion of the $CO_2$ evolution the solution obtained was stirred at 50° for 15 hrs. After cooling to room temperature the mixture was treated dropwise with 3.9 ml (0.060 mol) of propargylamine and stirred at room temperature for 1 hr. The orange solution was treated with 200 ml of ethyl acetate, whereby crystals separated. The suspension was suction filtered and the solution obtained was washed with water and concentrated. The crystalline residue and the crystals were recrystallized together from hot acetonitrile. There were obtained 6.31 g (68%) of (S)-9-oxo-12,12a-dihydro-9H,11H-azeto[2,1-c]imidazo[1,5-a][1,4]benzodiazepine-1-carboxylic acid prop-2-ynylamide as white crystals; m.p. 214°–215° and $[\alpha]_D^{20}$=−98.4° (DMF, c=1%).

b) A solution of 3.06 g (0.010 mol) of (S)-9-oxo-12,12a-dihydro-9H,11H-azeto[2,1-c]imidazo[1,5-a][1,4]benzodiazepine-1-carboxylic acid prop-2-ynylamide in 200 ml of acetic acid was treated with 3.36 g (0.015 mol) of N-iodosuccinimide while gassing with argon. After stirring at room temperature for 47 hrs. the dark brown suspension obtained was completely freed from the solvents and dried azeotropically several times with toluene. The red-brown solid residue was dissolved in 100 ml of THF, treated with 11.9 ml (0.0865 mol) of dipropylamine and stirred at room temperature for 17 hrs. The suspension obtained was completely freed from the solvents, the residue was partitioned between ethyl acetate and 1N aqueous hydrochloric acid and extracted. The aqueous-acidic phase was made basic and extracted with dichloromethane. The organic phase was concentrated, the brown product was chromatographed over basic Alox (grade III) with dichloromethane/ethyl acetate 4:1 as the eluent and recrystallized from hot isopropyl ether. There were obtained 1.09 g (27%) of (S)-1-(5-dipropylaminomethyl-oxazol-2-yl)-12,12a-dihydro-9H, 11H-azeto[2,1-c]imidazo[1,5-a][1,4]benzodiazepin-9-one as yellowish crystals; m.p. 132°–134° and $[\alpha]_D^{20}$=−187.8° (MeOH, c=1%).

c) 1.09 g (0.00269 mol) of (S)-1-(5-dipropylaminomethyloxazol-2-yl)-12,12a-dihydro-9H,11H-azeto[2,1-c]imidazo[1,5-a][1,4]benzodiazepin-9-one in 20 ml of ethyl acetate were treated with 0.80 ml (0.00296 mol) of 3N ethanolic hydrochloric acid at 0°. After stirring at 0° for 1 hr. the white suspension was suction filtered. The beige crystals were recrystallized from hot acetonitrile. There was obtained 0.71 g (60%) of (S)-1-(5-dipropylaminomethyl-oxazol-2-yl)-12,12a-dihydro-9H,11H-azeto[2,1-c]imidazo[1,5-a][1,4]benzodiazepin-9-one hydrochloride (1:1) as light yellowish crystals; m.p. 227°–230° and $[\alpha]_D^{20}$=−168.8° (MeOH, c=1%).

EXAMPLE 3 a) A suspension of 8.70 g (0.0298 mol) of 7-chloro-5-methyl-6-oxo-5,6-dihydro-4H-imidazo[1,5-a][1,4]benzodiazepine-3-carboxylic acid in 90 ml dimethylformamide in 90 ml of dimethylformamide was treated portionwise with 5.1 g (0.0313 mol) of carbonyldiimidazole while gassing with argon. After the addition of an additional 50 ml of DMF and after completion of the $CO_2$ evolution the yellow solution obtained was stirred at 50° for 1 hr. After cooling to room temperature the mixture was treated dropwise with 3.8 ml (0.060 mol) of propargylamine and stirred at room temperature for 17 hrs. The yellow solution was completely freed from the solvents and the crystalline residue was suspended in 150 ml of hot water, cooled to room temperature and filtered off under suction. There were obtained 9.40 g (96%) of 7-chloro-5-methyl-6-oxo-5,6-dihydro-4H-imidazo[1,5-a][1,4]benzodiazepine-3-carboxylic acid prop-2-ynylamide as white crystals; m.p. 241°–243° (dec.).

b) A solution of 3.28 g of (0.010 mol) of 7-chloro-5-methyl-6-oxo-5,6-dihydro-4H-imidazo[1,5-a][1,4] benzodiazepine-3-carboxylic acid prop-2-ynylamide in 60 ml of acetic acid was treated with 3.36 g (0.015 mol) of N-iodosuccinimide while gassing with argon. After stirring at room temperature for 67 hrs. the dark suspension obtained was completely freed from the solvents and dried azeotropically several times with toluene. The dark solid residue was dissolved in 100 ml of THF, treated with 13.7 ml (0.10 mol) of dipropylamine and stirred at room temperature for 3 hrs. The brown-orange suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated and the beige-brownish product was chromatographed twice: firstly over basic Alox (grade III) with dichloromethane/ethyl acetate 4:1 as the eluent, then over silica gel with dichloromethane/ methanol 98:2 as the eluent. There were obtained 1.2 g (28%) of 7-chloro-3-(5-dipropylaminomethyl-oxazol-2-yl)-5-methyl- 5,6-dihydro-4H-imidazo[1,5-a][1,4]benzodiazepin-6-one as a yellow viscous oil.

MS: m/e (% basic peak)=427 ($C_{22}H_{26}ClN_5O_2^+$, 1), 398 (9.5), 327 (100), 49 (14)

c) 1.2 g (0.0028 mol) of 7-chloro-3-(5-dipropylaminomethyloxazol-2-yl)-5-methyl-5,6-dihydro-4H-imidazo[1,5-a][1,4]-benzodiazepin-6-one in 80 ml of ethyl acetate were treated at 0° with 0.84 ml (0.0031 mol) of 3.7N ethanolic hydrochloric acid. After stirring at 0° for 15 minutes the white suspension was suction filtered. The yellowish crystals were dissolved in hot acetonitrile and recrystallized by the addition of ether. There were obtained 1.03 g (79%) of 7-chloro-3-(5-dipropylaminomethyl-oxazol-2-yl)-5-methyl-5,6-dihydro-4H-imidazo[1,5-a][1,4] benzodiazepin-6-one hydrochloride (1:1) as white crystals; m.p. 218°–210° (dec.).

EXAMPLE 4 a) A suspension of 4.0 g (0.0132 mol) of (S)-8-chloro-9-oxo-12,12a-dihydro-9H,11H-azeto[2,1-c]imidazo[1,5-a][1, 4]benzodiazepine-1-carboxylic acid in 50 ml of dimethylformamide was treated portionwise with 2.28 g (0.0138 mol) of carbonyldiimidazole while gassing with argon. After completion of the $CO_2$ evolution the yellow solution obtained was stirred at 50° for ½ hr. After cooling to room temperature the mixture was treated dropwise with 1.7 ml (0.026 mol) of propargylamine and stirred at room temperature for ½ hr. The yellow solution was completely freed from the solvents and the crystalline residue was suspended in 100 ml of hot water, cooled to 0° and filtered off under suction. There were obtained 3.85 g (86%) of (S)-8-chloro-9-oxo-12,12a-dihydro-9H,11H-azeto[2,1-c]imidazo[1,5-a] [1,4]benzodiazepine-1-carboxylic acid prop-2-ynylamide as white crystals; m.p. 244°–247° (dec.) and $[\alpha]_D^{20}$=+9.2° (DMF, c=1%).

b) A solution of 3.30 g (0.0098 mol) of (S)-8-chloro-9-oxo-12,12a-dihydro-9H,11H-azeto[2,1-c]imidazo[1,5-a][1, 4]benzodiazepine- 1-carboxylic acid prop-2-ynylamide in 60 ml of acetic acid was treated with 3.30 g (0.0147 mol) of N-iodosuccinimide while gassing with argon. After stirring at room temperature for 24 hrs. the dark brown suspension obtained was completely freed from the solvents and dried azeotropically several times with toluene. The dark viscous residue was dissolved in 60 ml of THF, treated with 11.9 ml (0.0865 mol) of dipropylamine and stirred at room temperature for 24 hrs. The suspension obtained was filtered and the solution was completely freed from the solvents, the residue was partitioned between ethyl acetate and dilute aqueous hydrochloric acid and extracted. The aqueous-acidic phase was made basic and extracted with ethyl acetate. The organic phase was concentrated and the residue was chromatographed over silica gel with dichloromethane/methanol 98:2 as the eluent. There were obtained 1.19 g (28%) of (S)-8-chloro-1-(5-dipropylaminomethyl-oxazol-2-yl)-12,12a-dihydro-9H,11H-azeto[2,1-c]imidazo[1,5-a][1,4] benzodiazepin-9-one as yellow crystals; m.p. 148°–151° (dec.) and $[\alpha]_D^{20}$=−101.7° (MeOH, c=1%)

c) 1.13 g (0.00257 mol) of (S)-8-chloro-1-(5-dipropylaminomethyl-oxazol-2-yl)-12,12a-dihydro-9H, 11H-azeto[2,1-c]-imidazo[1,5-a][1,4]benzodiazepin-9-one in 50 ml ethanol were treated at 0° with 0.73 ml (0.00270 mol) of 3.7N ethanolic hydrochloric acid. A suspension was obtained after stirring at 0° for ¼ hr. It was treated with 50 ml of ether and suction filtered. There was obtained 1.0 g (82%) of (S)-8-chloro-1-(5-dipropylaminomethyl-oxazol-2-yl)-12,12a-dihydro-9H,11H-azeto[2,1-c]imidazo[1,5-a][1,4]benzodiazepin-9-one hydrochloride (1:1) as white crystals; m.p. 237°–240° (dec.) and $[\alpha]_D^{20}$=−163.4° (H$_2$O, c=1%).

EXAMPLE 5 a) A solution of 1.07 g (0.003 mol) of (S)-8-chloro-9-oxo-11,12,13,13a-tetrahydro-9H-imidazo[1,5-a]pyrrolo[2,1-c][1,4]-benzodiazepine-1-carboxylic acid prop-2-ynylamide in 10 ml of acetic acid was treated with 1.01 g (0.0045 mol) of N-iodosuccinimide. After stirring at room temperature for 12 hrs. the mixture was heated to 50° for a further 4 hrs. The dark suspension obtained was completely freed from solvent in a vacuum and dried azeotropically several times with toluene. The brown residue was dissolved in 10 ml of THF, treated at room temperature with 10 ml (0.073 mol) of dipropylamine and stirred at 50° for 2 hrs. The suspension obtained was completely freed from the solvents and the residue was partitioned between ethyl acetate and 1N aqueous hydrochloric acid and extracted. The acidic phase was made basic and extracted with ethyl acetate. The organic phase was concentrated, the pale brown product was chromatographed over silica gel with dichloromethane/methanol 95:5 as the eluent and digested with diethyl ether. There was obtained 0.65 g (48%) of (S)-8-chloro-1-(5-dipropylaminomethyl-oxazol-2-yl)-11,12,13,13a-tetrahydro-9H-imidazo[1,5-a]pyrrolo[2,1-c][1,4]-benzodiazepin-9-one; $[\alpha]_D^{20}$=+11.5° (MeOH, c=1%)

MS: m/e (% basic peak)=453 (1, $C_{24}H_{28}ClN_5O_2$+), 424 (10), 353 (100), 114 (9).

b) 0.375 g (0.00083 mol) of (S)-8-chloro-1-(5-dipropylaminomethyl-oxazol-2-yl)-11,12,13,13a-tetrahydro-9H-imidazo[1,5-a]pyrrolo[2,1-c][1,4]-benzodiazepin-9-one was treated with 7.85 ml of 0.1N aqueous hydrochloric acid and stirred for ½ hr. Subsequently, the mixture was filtered and the filtrate was lyophilized. There was thus isolated 0.395 g of (S)-8-chloro-1-(5-dipropylaminomethyl-oxazol-2-yl)-11,12,13,13a-tetrahydro-9H-imidazo[1,5-a]pyrrolo[2,1-c][1,4]-benzodiazepin-9-one hydrochloride (1:1).

MS: m/e (% basic peak)=424 ($C_{24}H_{28}ClN_5O_2$+—$C_2H_5$, 10), 353 (100), 114 (8)

EXAMPLE 6 a) A solution of 7.95 g (0.0224 mol) of (S)-8-chloro-9-oxo-11,12,13,13a-tetrahydro-9H-imidazo[1,5-a]pyrrolo[2,1-c][1,4]benzodiazepine-1-carboxylic acid prop-2-ynylamide in 200 ml of acetic acid was treated with 7.56 g (0.0336 mol) of N-iodosuccinimide while gassing with argon. After stirring at room temperature for 19 hrs. and at 50° for 4 hrs. the dark brown suspension obtained was completely freed from the solvents and dried azeotropically several times with toluene. The red-brown solid residue was dissolved in 100 ml of THF, treated with 23.9 ml (0.194 mol) of diallylamine and stirred at room temperature for 48 hrs. The solution obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the dark brown product was chromatographed over basic Alox (grade III) with dichloromethane/ethyl acetate 4:1 as the eluent and recrystallized from hot isopropyl ether. There were obtained 2.89 g (29%) of (S)-8-chloro-1-(5-diallylaminomethyl-oxazol-2-yl)-11,12,13,13a-tetrahydro-9H-imidazo[1,5-a]pyrrolo[2,1-c][1,4]benzodiazepin-9-one as a yellow foam; $[\alpha]_D^{20}$=+11.3° (MeOH, c=1%).

b) 1.15 g (0.00255 mol) of (S)-8-chloro-1-(5-diallylaminomethyl-oxazol-2-yl)-11,12,13,13a-tetrahydro-9H-imidazo[1,5-a]pyrrolo[2,1-c][1,4]benzodiazepin-9-one in 20 ml of ethanol were treated with 0.53 ml (0.00253 mol) of 4.78N ethanolic hydrochloric acid at 0°. After stirring at 0° for 10 minutes the colorless solution was completely freed from the solvents. The residue was dissolved in hot ethanol and recrystallized by the addition of ether. There was obtained 0.9 g (78%) of (S)-8-chloro-1-(5-diallylaminomethyl-oxazol-2-yl)-11,12,13,13a-tetrahydro-9H-imidazo[1,5-a]pyrrolo[2,1-c][1,4]benzodiazepin-9-one hydrochloride (1:1) as beige crystals; m.p. 169°–171° and $[\alpha]_D^{20}$=+7.70 (MeOH, c=1%).

EXAMPLE 7 a) A suspension of 250 g (0.908 mol) of 8-fluoro-5-methyl-6-oxo-5,6-dihydro-4H-imidazo[1,5-a][1,4]benzodiazepine-3-carboxylic acid in 2500 ml of dimethylformamide was treated portionwise with 155 g (0.953 mol) of carbonyldiimidazole while gassing with argon. After completion of the CO$_2$ evolution the white suspension obtained was stirred at 50° for ½ hr. After cooling to room temperature the mixture was treated within ½ hr. with 116 ml (1.82 mol) of propargylamine and stirred at room temperature for 1 hr. The deep yellow solution was completely freed from the solvents and the crystalline residue was suspended in 500 ml of hot ethanol, cooled to 0° and filtered off under suction. There were obtained 254 g (90%) of 8-fluoro-5-methyl-6-oxo-5,6-dihydro-4H-imidazo[1,5-a][1,4]-benzodiazepine-3-carboxylic acid prop-2-ynylamide as white crystals; m.p. 205°–206°.

b) A solution of 1 5.6 g (0.050 mol) of 8-fluoro-5-methyl-6-oxo-5,6-dihydro-4H-imidazo[1,5-a][1,4]benzodiazepine-3-carboxylic acid prop-2-ynylamide in 300 ml of acetic acid was treated with 16.9 g (0.075 mol) of N-iodosuccinimide while gassing with argon. After stirring at room temperature for 106 hrs. the dark suspension obtained was completely freed from the solvents and dried azeotropically several times with toluene. The dark brown solid residue was dissolved in 500 ml of THF.

125 ml of this crude solution of 8-fluoro-3-(5-iodomethyl-oxazol-2-yl)-5-methyl-5,6-dihydro-4H-imidazo[1,5-a][1,4]benzodiazepin-6-one were treated with 11.3 ml (0.109 mol) of diethylamine and stirred at room temperature for 20 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the orange-brownish product was chromatographed over silica gel with ethyl acetate/methanol 17:3 as the eluent and recrystallized from hot ethyl acetate. There was obtained 0.75 g (16%) of 3-(5-diethylaminomethyloxazol-2-yl)-8-fluoro-5-methyl-5,6-dihydro-4H-imidazo[1,5-a][1,4]benzodiazepin-6-one as light beige crystals; m.p. 182°–184°. A further 0.39 g of yellowish crystals was obtained from the mother liquor.

c) 0.89 g (0.00232 mol) of 3-(5-diethylaminomethyl-oxazol-2-yl)-8-fluoro-5-methyl-5,6-dihydro-4H-imidazo[1,5-a][1,4]-benzodiazepin-6-one in 50 ml of ethyl acetate was treated with 0.66 ml (0.00244 mol) of 3.7N ethanolic hydrochloric acid. After stirring at 0° for ½ hr. the white suspension was suction filtered. There was obtained 0.94 g (97%) of 3-(5-diethylaminomethyl-oxazol-2-yl)-8-fluoro-5-methyl-5,6-dihydro-4H-imidazo[1,5-a][1,4]benzodiazepin-6-one hydrochloride (1:1) as whitish crystals; m.p. 247°–250° (dec.).

EXAMPLE 8 a) A solution of 10 g (0.032 mol) of 8-fluoro-5-methyl-6-oxo-5,6-dihydro-4H-imidazo[1,5-a][1,4]benzodiazepine-3-carboxylic acid prop-2-ynylamide in 200 ml of acetic acid was treated with 10.8 g (0.048 mol) of N-iodosuccinimide while gassing with argon. After stirring at room temperature for 90 hrs. the dark suspension obtained was completely freed from the solvents and dried azeotropically several times with toluene. The dark residue was dissolved in 200 ml of THF, treated with 23 ml (0.278 mol) of propylamine and stirred at room temperature for 5 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated and the orange crystalline product was chromatographed twice; firstly over basic Alox (grade III) with ethyl acetate/methanol 4:1 as the eluent, then over silica gel with dichloromethane/methanol 9:1 as the eluent. There were obtained 1.17 g (10%) of 8-fluoro-5-methyl-3-(5-propylaminomethyl-oxazol-2-yl)-5,6-dihydro-4H-imidazo[1,5-a][1,4]benzodiazepin-6-one as yellowish crystals; m.p. 134°–136°.

b) 1.14 g (0.0031 mol) of 8-fluoro-5-methyl-3-(5-propylaminomethyl-oxazol-2-yl)-5,6-dihydro-4H-imidazo[1,5-a][1,4]-benzodiazepin-6-one in 50 ml of ethanol were treated with 0.84 ml (0.0031 mol) of 3.7N ethanolic hydrochloric acid. After stirring at 0° for ½ hr. the white suspension was suction filtered. There was obtained 0.93 g (74%) of 8-fluoro-5-methyl- 3-(5-propylaminomethyl-oxazol-2-yl)-5,6-dihydro-4H-imidazo-[1,5-a][1,4]benzodiazepin-6-one hydrochloride (1:1) as white crystals; m.p. 178°–181° (dec.).

EXAMPLE 9 a) A solution of 3.12 g (0.010 mol) of 8-fluoro-5-methyl-6-oxo-5,6-dihydro-4H-imidazo[1,5-a][1,4]benzodiazepine-3-carboxylic acid prop-2-ynylamide in 200 ml of acetic acid was treated with 3.36 g (0.015 mol) of N-iodosuccinimide while gassing with argon. After stirring at room temperature for 39 hrs. the dark brown suspension obtained was completely freed from the solvents and dried azeotropically several times with toluene. The brown residue was dissolved in 100 ml of THF, treated with 11.9 ml (0.0865 mol) of dipropylamine and stirred at room temperature for 22 hrs. The brown solution obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the orange-brownish product was chromatographed over basic Alox (grade III) with dichloromethane/ethyl acetate 4:1 as the eluent and recrystallized from hot isopropyl ether. There was obtained 1.0 g (24%) of 3-(5-dipropylaminomethyl-oxazol-2-yl)-8-fluoro-5-methyl-5,6-dihydro-4H-imidazo[1,5-a][1,4]benzodiazepin-6-one as yellowish crystals; m.p. 123°–125°.

b) 1.0 g (0.00243 mol) of 3-(5-dipropylaminomethyl-oxazol-2-yl)-8-fluoro-5-methyl-5,6-dihydro-4H-imidazo[1,5-a][1,4]benzodiazepin-6-one in 50 ml of ethyl acetate was treated with 0.56 ml (0.00267 mol) of 4.78N ethanolic hydrochloric acid. After stirring at 0° for 1 hr. the white suspension was suction filtered. There was obtained 0.96 g (88%) of 3-(5-dipropylaminomethyl-oxazol-2-yl)-8-fluoro-5-methyl-5,6-dihydro-4H-imidazo[1,5-a][1,4]benzodiazepin-6-one hydrochloride (1:1) as white crystals; m.p. 246°–248°.

EXAMPLE 10 a) 125 ml of a crude THF solution of 8-fluoro-3-(5-iodomethyl-oxazol-2-yl)-5-methyl-5,6-dihydro-4H-imidazo[1,5-a][1,4]benzodiazepin-6-one (prepared from 15.6 g (0.050 mol) of 8-fluoro-5-methyl-6-oxo-5,6-dihydro-4H-imidazo[1,5-a][1,4]-benzodiazepine-3-carboxylic acid prop-2-ynylamide and 16.9 g (0.075 mol) of N-iodosuccinimide in 300 ml of acetic acid, subsequently completely freed from the solvents, dried azeotropically several times with toluene and dissolved in 500 ml of THF) were treated with 15.4 ml (0.109 mol) of diisopropylamine and stirred at room temperature for 42 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated and the brownish product was chromatographed over silica gel with dichloromethane/methanol 39:1 as the eluent. There was obtained 0.83 g (1 6%) of 3-(5-diisopropylaminomethyl-oxazol-2-yl)-8-fluoro-5-methyl-5,6-dihydro-4H-imidazo[1,5-a][1,4]benzodiazepin-6-one as yellowish crystals; m.p. 176°–178°.

b) 0.82 g (0.0020 mol) of 3-(5-diisopropylaminomethyl-oxazol-2-yl)-8-fluoro-5-methyl-5,6-dihydro-4H-imidazo[1,5-a][1,4]benzodiazepin-6-one in 50 ml of ethyl acetate was treated with 0.57 ml (0.0021 mol) of 3.7N ethanolic hydrochloric acid. After stirring at 0° for ½ hr. the white suspension was suction filtered. There was obtained 0.82 g (91%) of 3-(5-diisopropylaminomethyl-oxazol-2-yl)-8-fluoro-5-methyl-5,6-dihydro-4H-imidazo[1,5-a][1,4]benzodiazepin-6-one hydrochloride (1:1) as whitish crystals; m.p. 232°–235° (dec.).

EXAMPLE 11 a) 125 ml of a crude THF solution of 8-fluoro-3-(5-iodomethyl-oxazol-2-yl)-5-methyl-5,6-dihydro-4H-imidazo[1,5-a][1,4]benzodiazepin-6-one (prepared from 15.6 g (0.050 mol) of 8-fluoro-5-methyl-6-oxo-5,6-dihydro-4H-imidazo[1,5-a][1,4]-benzodiazepine-3-carboxylic acid prop-2-ynylamide and 16.9 g (0.075 mol) of N-iodosuccinimide, subsequently completely freed from the solvents, dried azeotropically several times with toluene and dissolved in 500 ml of THF) were treated with 18.5 ml (0.109 mol) of dibutylamine and stirred at room temperature for 42 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated and the orange product was chromatographed over silica gel with dichloromethane/methanol 39:1 as the eluent. There was obtained 0.83 g (15%) of 3-(5-dibutylaminomethyl-oxazol-2-yl)-8-fluoro-5-methyl-5,6-dihydro-4H-imidazo[1,5-a][1,4]benzodiazepin-6-one as yellowish crystals; m.p. 100°–103° (dec.).

b) 0.82 g (0.00187 mol) of 3-(5-dibutylaminomethyl-oxazol-2-yl)-8-fluoro-5-methyl-5,6-dihydro-4H-imidazo[1,5-a][1,4]-benzodiazepin-6-one in 50 ml of acetic acid was treated with 0.53 ml (0.00196 mol) of 3.7N ethanolic hydrochloric acid. After stirring at 0° for ½ hr. the white suspension was suction filtered. There was obtained 0.84 g (94%) of 3-(5-dibutylaminomethyl-oxazol-2-yl)-8-fluoro-5-methyl-5,6-dihydro-4H-imidazo[1,5-a][1,4]benzodiazepin-6-one hydrochloride (1:1) as white crystals; m.p. 251°–254° (dec.).

EXAMPLE 12 a) 125 ml of a crude THF solution of 8-fluoro-3-(5-iodomethyl-oxazol-2-yl)-5-methyl-5,6-dihydro-4H-imidazo[1,5-a][1,4]benzodiazepin-6-one (prepared from 15.6 g (0.050 mol) of 8-fluoro-5-methyl-6-oxo-5,6-dihydro-4H-imidazo[1,5-a][1,4]-benzodiazepine-3-carboxylic acid prop-2-ynylamide and 16.9 g (0.075 mol) of N-iodosuccinimide, subsequently completely freed from the solvents, dried azeotropically several times with toluene and dissolved in 500 ml of THF) were treated with 10.7 ml (0.109 mol) of piperidine and stirred at room temperature for 3 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the beige-brown product was chromatographed over silica gel with ethyl acetate/methanol 4:1 as the eluent and recrystallized from hot ethyl acetate. There was obtained 0.85 g (17%) of 8-fluoro-5-methyl-3-(5-piperidin-1-ylmethyl-oxazol-2-yl)-5,6-dihydro-4H-imidazo[1,5-a][1,4]benzodiazepin-6-one as yellowish crystals; m.p. 191°–193°.

b) 0.84 g (0.00212 mol) of 8-fluoro-5-methyl-3-(5-piperidin-1-ylmethyl-oxazol-2-yl)-5,6-dihydro-4H-imidazo[1,5-a][1,4]-benzodiazepin-6-one was dissolved in 30 ml of hot ethanol and treated at 50° with 0.60 ml (0.00227 mol) of 3.7N ethanolic hydrochloric acid. After stirring at 0° for 1 hr. the white suspension was suction filtered. There was obtained 0.80 g (87%) of 8-fluoro-5-methyl-3-(5-piperidin-1-ylmethyl-oxazol-2-yl)-5,6-dihydro-4H-imidazo[1,5-a][1,4]benzodiazepin-6-one hydrochloride (1:1) as yellowish crystals; m.p. 276°–280° (dec.).

EXAMPLE 13 a) A suspension of 3.72 g (0.012 mol) of 7-chloro-8-fluoro-5-methyl-6-oxo-5,6-dihydro-4H-imidazo[1,5-a][1,4]benzodiazepine-3-carboxylic acid in 40 ml of dimethylformamide was treated portionwise with 2.04 g (0.0126 mol) of carbonyldiimidazole while gassing with argon. After completion of the $CO_2$ evolution the suspension obtained was stirred at 60° for 2 hrs. After cooling to room temperature the solution, which was now yellow, was treated dropwise with 1.14 ml (0.024 mol) of propargylamine and stirred at room temperature for 1 hr. The yellow solution was completely freed from the solvents and the crystalline residue was suspended in 150 ml of hot water, cooled to room temperature and filtered off under suction. There were obtained 3.49 g (84%) of 7-chloro-8-fluoro-5-methyl-6-oxo-5,6-dihydro-4H-imidazo[1,5-a][1,4]benzodiazepine-3-carboxylic acid prop-2-ynylamide as beige crystals; m.p. 235°–237°.

b) A solution of 3.49 g (0.010 mol) of 7-chloro-8-fluoro-5-methyl-6-oxo-5,6-dihydro-4H-imidazo[1,5-a][1,4]benzodiazepine- 3-carboxylic acid prop-2-ynylamide in 200 ml of acetic acid was treated with 3.38 g (0.0151 mol) of N-iodosuccinimide while gassing with argon. After stirring at room temperature for 53 hrs. the dark suspension obtained was completely freed from the solvents and dried azeotropically several times with toluene. The red-brown residue was dissolved in 100 ml of THF, treated with 11.9 ml (0.087 mol) of dipropylamine and stirred at room temperature for 16 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated and the yellow-brown product was chromatographed over basic Alox (grade III) with dichloromethane/ethyl acetate 17:3 as the eluent. There were obtained 1.1 g (25%) of 7-chloro-3-(5-dipropylaminomethyl-oxazol-2-yl)-8-fluoro-5-methyl-5,6-dihydro-4H-imidazo[1,5-a][1,4]benzodiazepin-6-one as a yellow foam. A sample was recrystallized from isopropyl ether; m.p. 110°–112°.

c) 1.1 g (0.00247 mol) of 7-chloro-3-(5-dipropylaminomethyl-oxazol-2-yl)-8-fluoro-5-methyl-5,6-dihydro-4H-imidazo[1,5-a][1,4 ]benzodiazepin-6-one in 50 ml of ethyl acetate were treated with 0.50 ml (0.00185 mol) of 3.7N ethanolic hydrochloric acid. After stirring at 0° for 1 hr. the white suspension was suction filtered. There was obtained 0.97 g (81%) of 7-chloro-3-(5-dipropylaminomethyl-oxazol-2-yl)-8-fluoro-5-methyl-5,6-dihydro-4H-imidazo[1,5-a][1,4]benzodiazepin-6-one hydrochloride (1:1) as white crystals; m.p. 243°–245°.

EXAMPLE 14 a) A suspension of 4.35 g (0.0165 mol) of 5-methyl-6-oxo-5,6-dihydro-4H-imidazo[1,5-a]thieno[2,3-f][1,4]diazepine-3-carboxylic acid in 90 ml of dimethylformamide was treated portionwise with 2.80 g (0.0173 mol) of carbonyldiimidazole while gassing with argon. After completion of the $CO_2$ evolution the yellow solution obtained was stirred at 50° for ½ hr. After cooling to room temperature the mixture was treated dropwise with 2.1 ml (0.033 mol) of propargylamine and stirred at 70° for 1 hr. The yellow solution was completely freed from the solvents and the crystalline residue was suspended in 150 ml of hot water, cooled to room temperature and filtered off under suction. There were obtained 4.6 g (93%) of 5-methyl-6-oxo-5,6-dihydro-4H-imidazo[1,5-a]thieno[2,3-f][1,4]diazepine-3-carboxylic acid prop-2-ynylamide as white crystals; m.p. 275°–277°.

b) A solution of 3.0 g (0.010 mol) of 5-methyl-6-oxo-5,6-dihydro-4H-imidazo[1,5-a]thieno[2,3-f][1,4]diazepine-3-carboxylic acid prop-2-ynylamide in 180 ml of acetic acid was treated with 3.36 g (0.015 mol) of N-iodosuccinimide while gassing with argon. After stirring at room temperature for 45 hrs. the dark suspension obtained was completely freed from the solvents and dried azeotropically several times with toluene. The black-brown solid residue was suspended in 200 ml of THF, treated with 13.7 ml (0.10 mol) of dipropylamine and stirred at room temperature for 17 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the orange-brownish product was chromatographed over basic Alox (grade III) with dichloromethane/ethyl acetate 4:1 as the eluent and recrystallized from hot isopropyl ether. There were obtained 1.14 g (29%) of 3-(5-dipropylaminomethyl-oxazol-2-yl)-5-methyl-5,6-dihydro-4H-imidazo[1,5-a]thieno[2,3-f][1,4]-diazepin-6-one as yellowish crystals; m.p. 142°–144°.

c) 1.13 g (0.00283 mol) of 3-(5-dipropylaminomethyl-oxazol-2-yl)-5-methyl-5,6-dihydro-4H-imidazo[1,5-a]

thieno[2,3-f][1,4]-diazepin-6-one in 50 ml of ethyl acetate were treated with 0.84 ml (0.00311 mol) of 3.7N ethanolic hydrochloric acid. After stirring at 0° for ½ hr. the suspension was suction filtered. The yellowish crystals were dissolved in hot acetonitrile and recrystallized by the addition of ether. There were obtained 1.05 g (85%) of 3-(5-dipropylaminomethyl-oxazol-2-yl)-5-methyl-5,6-dihydro-4H-imidazo[1,5-a]thieno[2,3-f][1,4]diazepin- 6-one hydrochloride (1:1) as light beige crystals; m.p. 237°–241° (dec.).

EXAMPLE 15 a) A solution of 26.9 g (0.171 mol) of 2H-thieno-[3,2-d][1,3]-oxazine-2,4(1H)-dione and 16.1 g (0.171 mol) of L-azetidine-2-carboxylic acid in 200 ml of dimethylformamide and 40 ml of acetic acid was stirred at 120° for 3 hrs. The brown solution was evaporated and the brown residue obtained was crystallised from ethanol. There were obtained 15.2 g (43%) of (S)-6,7-dihydroazeto[1,2-a]thieno[3,2-e][1,4]diazepine-5,9(4H,5aH)-dione as colorless crystals; m.p. 274°.

b) To a suspension of 1.92 g (0.044 mol) of NaH (55%, washed with hexane) in 5 ml of dimethylformamide was added dropwise at −30° a solution of 8.32 g (0.040 mol) of (S)-6,7-dihydroaceto-[1,2-a]thieno[3,2-e][1,4]diazepine-5,9 (4H,5aH)-dione in 45 ml of dimethylformamide and the mixture was stirred at −30° for 40 minutes. After cooling to −60° a solution of 8.26 ml (0.040 mol) of phosphoric acid diphenyl ester chloride in 3 ml of dimethylformamide was added dropwise in such a manner that the temperature did not rise above −45°. Subsequently, the mixture was stirred for a further ½ hr.

In the meanwhile, 4.92 g (0.044 mol) of potassium tert.-butylate were dissolved in 20 ml of dimethylformamide and treated at −60° with 4.7 ml (0.0428 mol) of ethyl isocyanoacetate (95%). The resulting solution was treated dropwise at −70° with the reaction mixture obtained above via a dropping funnel cooled to −40°. The dark brown viscous solution obtained was stirred at −60° for 1 hr. After neutralization with 4.8 ml of acetic acid at −40° the mixture was poured on to 300 ml of icewater and extracted five times with dichloromethane. The combined organic phases were dried over sodium sulphate, filtered and evaporated. The pale brown residue obtained was recrystallized from ethanol. There were obtained 8.12 g (67%) of ethyl (S)-8-oxo-11,11a-dihydro-8H,10H-azeto[1,2-a]imidazo[5,1-c]thieno-[3,2-e][1,4]diazepine-1-carboxylate as colorless crystals; m.p. 188°–191°.

c) 13.9 ml (0.0556 mol) of 4N sodium hydroxide solution were added dropwise to a suspension of 13.5 g (0.0445 mol) of (S)-8-oxo-11,11a-dihydro-8H,10H-azeto[1,2-a]imidazo[5,1-c]thieno-[3,2-e][1,4]diazepine-1-carboxylate in 10 ml of ethanol and 16 ml of water and the mixture was heated at reflux for ½ hr. Subsequently, the ethanol was distilled off. The aqueous phase was washed twice with dichloromethane and adjusted to pH=3 with 4N hydrochloric acid. The resulting precipitate was filtered off, washed with water, ethanol and subsequently with diethyl ether. There were obtained 10.8 g (88%) of (S)-8-oxo-11,11a-dihydro-8H,10H-azeto[1,2-a]imidazo[5,1-c]thieno[3,2-e][1,4]-diazepine-1-carboxylic acid as a colorless powder; m.p. 260° (dec.).

d) A suspension of 3.60 g (0.013 mol) of (S)-8-oxo-11,11a-dihydro-8H,10H-azeto[1,2-a]imidazo[5,1-c]thieno[3,2-e][1,4]-diazepine-1-carboxylic acid in 40 ml of dimethylformamide was treated portionwise with 2.22 g (0.0137 mol) of carbonyldiimidazole while gassing with argon. After completion of the $CO_2$ evolution the yellow solution obtained was stirred at 50° for ½ hr. After cooling to room temperature the mixture was treated dropwise with 1.66 ml (0.026 mol) of propargylamine and stirred at room temperature for 2 hrs. The yellow solution was completely freed from the solvents and the crystalline residue was suspended in 150 ml of hot water, cooled to room temperature and filtered off under suction. There were obtained 2.7 g (67%) of (S)-8-oxo-11,11a-dihydro-8H,10H-azeto[1,2-a]imidazo[5,1-c]thieno[3,2-e][1,4]diazepine-1-carboxylic acid prop-2-ynylamide as white crystals; m.p. 233°–235° and $[\alpha]_D^{20}$= −22.9° (DMF, c=1%).

e) A solution of 3.10 g (0.00992 mol) of (S)-8-oxo-11,11a-dihydro-8H,10H-azeto[1,2-a]imidazo[5,1-c]thieno[3,2-e][1,4]-diazepine-1-carboxylic acid prop-2-ynylamide in 60 ml of acetic acid was treated with 3.35 g (0.0149 mol) of N-iodosuccinimide while gassing with argon. After stirring at room temperature for 24 hrs. the dark suspension obtained was completely freed from the solvents and dried azeotropically several times with toluene. The dark residue was dissolved in 60 ml of THF, treated with 7.1 ml (0.0863 mol) of propylamine and stirred at room temperature for 6 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated and the dark product was chromatographed over silica gel which dichloromethane/methanol 49:1 as the eluent. There was obtained 0.29 g (8%) of (S)-1-(5-propylaminomethyl-oxazol-2-yl)-11,11 a-dihydro-8H,10H-azeto[1,2-a]imidazo[5,1-c]thieno[3,2-e][1,4]diazepin-8-one as yellowish crystals; m.p. 145°–147°.

f) 0.23 g (0.00062 mol) of (S)-1-(5-propylaminomethyl-oxazol-2-yl)-11,11a-dihydro-8H,10H-azeto[1,2-a]imidazo[5,1-c]thieno[3,2-e][1,4]diazepin-8-one in 15 ml of ethanol was treated with 0.18 ml (0.00065 mol) of 3.7N ethanolic hydrochloric acid. The yellow solution was concentrated to 5 ml and treated with 15 ml of ethyl acetate. After stirring at 0° for ½ hr. the suspension was suction filtered. There was obtained 0.19 g (76%) of (S)-1-(5-propylaminomethyl-oxazol-2-yl)-11,11a-dihydro-8H,10H-azeto[1,2-a]imidazo[5,1-c]thieno[3,2-e][1,4]diazepin-8-one hydrochloride (1:1) as white crystals; m.p. 218°–220° (dec.) and $[\alpha]_D^{20}$=−285.3° ($H_2O$, c=3%).

EXAMPLE 16 a) A solution of 2.60 g (0.00832 mol) of (S)-8-oxo-11,11a-dihydro-8H,10H-azeto[1,2-a]imidazo[5,1-c]thieno[3,2-e][1,4]-diazepine-1-carboxylic acid prop-2-ynylamide in 60 ml of acetic acid was treated with 2.8 g (0.0125 mol) of N-iodosuccinimide while gassing with argon. After stirring at room temperature for 46 hrs. the dark suspension obtained was completely freed from the solvents and dried azeotropically several times with toluene. The dark solid residue was suspended in 100 ml of THF, treated with 11.4 ml (0.0832 mol) of dipropylamine and stirred at room temperature for 18 hrs. The suspension obtained was completely freed from the solvents, the residue was partitioned between ethyl acetate and 1N aqueous hydrochloric acid and extracted. The aqueous-acidic phase was made basic and extracted with ethyl acetate. The organic phase was concentrated, the orange-brownish product was chromatographed over basic Alox (grade III) with dichloromethane/ethyl acetate 4:1 as the eluent and recrystallized from hot isopropyl ether. There was obtained 1.0 g (25%) of (S)-1-(5-dipropylaminomethyl-oxazol-2-yl)-11,11a-dihydro-8H, 10H-azeto[1,2-a]imidazo[5,1-c]thieno[3,2-e][1,4]-diazepin-8-one as yellowish crystals; m.p. 133°–135° and $[\alpha]_D^{20}$=−32.3° (CHCl$_3$, c=1%).

b) 0.92 g (0.00224 mol) of (S)-1-(5-dipropylaminomethyl-oxazol-2-yl)-11,11a-dihydro-8H,10H-azeto[1,2-a]imidazo[5,1-c]thieno[3,2-e][1,4]diazepin-8-one in 50 ml of ethyl acetate was treated with 0.67 ml (0.00246 mol) of 3.7N ethanolic hydrochloric acid. After stirring at 0° for ½ hr. the suspension was suction filtered. The yellowish crystals were dissolved in hot acetonitrile and recrystallized by the addition of ether. There was obtained 0.88 g (88%) of (S)-1-(5-dipropylaminomethyl-oxazol-2-yl)-11,11a-dihydro-8H,10H-azeto[1,2-a]imidazo[5,1-c]thieno[3,2-e][1,4]diazepin-8-one hydrochloride (1:1) as whitish crystals; m.p. 233°–236° (dec.) and $[\alpha]_D^{20}$=−29.2° (H$_2$O, c=1%).

EXAMPLE 17 a) A stream of hydrogen sulphide was passed for 1 hr. through a solution of 10.2 g (0.429 mol) of 5-methyl-6-oxo-5,6-dihydro-4H-imidazo[1,5-a][1,4]benzodiazepine-3-carbonitrile in 250 ml of pyridine and 2.5 ml of triethylamine. The green solution was left to stand for 48 hrs., then de-gassed with a stream of nitrogen and subsequently completely freed from the solvents. The residue was partitioned between dichloromethane and water and the suspension obtained was suction filtered. There were obtained 9.0 g (87%) of 5-methyl-6-oxo-5,6-dihydro-4H-imidazo[1,5-a][1,4]benzodiazepine-3-thiocarboxamide as yellow crystals. A sample was recrystallized from methanol and gave pale yellow crystals; m.p. 295°–297°.

b) A yellow suspension of 8.60 g (0.0316 mol) of 5-methyl-6-oxo-5,6-dihydro-4H-imidazo[1,5-a][1,4]benzodiazepine-3-thiocarboxamide in 200 ml of dioxan was treated with 4.41 g (0.0347 mol) of 1,3-dichloro-2-propanone. The suspension was boiled at reflux for 3 hrs., cooled and filtered. The solution was boiled at reflux for a further 16 hrs., cooled and suction filtered. The product was recrystallized from hot acetonitrile. There were obtained 5.4 g (65%) of 3-(4-chloromethyl-thiazol-2-yl)-5-methyl-5,6-dihydro-4H-imidazo[1,5-a][1,4]benzodiazepin-6-one as white crystals. An analytical sample could be obtained from the mother liquor after chromatography (silica gel, cyclohexane/ethyl acetate 1:1) and recrystallization (acetonitrile); m.p. 248°–249°.

c) A solution of 1.0 g (0.0029 mol) of 3-(4-chloromethyl-thiazol-2-yl)-5-methyl-5,6-dihydro-4H-imidazo[1,5-a][1,4]-benzodiazepin-6-one in 60 ml of tetrahydrofuran was treated with 7.9 ml (0.058 mol) of dipropylamine. After stirring at reflux for 16 hrs. the solution obtained was completely freed from the solvents. The residue was chromatographed over silica gel with ethyl acetate and the eluent and recrystallized from hot isopropyl ether. There was obtained 0.67 g (56%) of 3-(4-dipropylaminomethyl-thiazol-2-yl)-5-methyl-5,6-dihydro-4H-imidazo[1,5-a][1,4] benzodiazepin-6-one as white crystals; m.p. 111°–112°.

d) 0.90 g (0.00219 mol) of 3-(4-dipropylaminomethyl-thiazol-2-yl)-5-methyl-5,6-dihydro-4H-imidazo[1,5-a][1,4] benzodiazepin-6-one in 25 ml of ethanol was treated with 0.59 ml (0.00218 mol) of 3.7N ethanolic hydrochloric acid. After stirring at room temperature for 10 minutes the solution obtained was completely freed from the solvents. The residue was recrystallized from ethanol/ether. There was obtained 0.90 g (92%) of 3-(4-dipropylaminomethyl-thiazol-2-yl)-5-methyl-5,6-dihydro-4H-imidazo[1,5-a][1,4] benzodiazepin-6-one hydrochloride (1:1) as white crystals; m.p. 216°–218°.

EXAMPLE 18 a) 192 g (0.715 mol) of (S)-9-oxo-12,12a-dihydro-9H,11H-azeto[2,1-c]imidazo[1,5-a][1,4]benzodiazepine-1-carboxylic acid were suspended in 900 ml of dimethylformamide, treated at room temperature with 116 g (0.715 mol) of carbonyldiimidazole and stirred at 50° for ½ hr. Then, 173 ml of 25% ammonia were added dropwise at 25°–30° within ½ hr. After stirring for ½ hr the reaction mixture was concentrated and the residue was dissolved in 500 ml of alcohol. After the addition of 250 ml of ether the solution was cooled to 0° and the suspension was suction filtered. There were obtained 133.6 g (69%) of (S)-9-oxo-12,12a-dihydro-9H,11H-azeto[2,1-c]imidazo[1,5-a][1,4]-benzodiazepine-1-carboxamide; m.p. 228°–230°.

b) A suspension of 78 g (0.78 g mol) of (S)-9-oxo-12,12a-dihydro-9H,11H-azeto[2,1-c]imidazo[1,5-a][1,4] benzodiazepine-1-carboxamide in a mixture of 380 ml of dioxan and 68 ml of pyridine was treated dropwise at 0° with 59 ml (0.424 mol) of trifluoroacetic anhydride. The suspension was stirred at 50° for 2 hrs., cooled and poured on to 2 l of ice-water. After vigorous stirring the suspension was suction filtered. There were obtained 60 g (82%) of (S)-9-oxo-12,12a-dihydro-9H,11H-azeto[2,1-c]imidazo[1,5-a][1,4]benzodiazepine-1-carbonitrile; m.p. 232°–234°.

c) A stream of hydrogen sulphide was conducted for ½ hr. through a solution of 5.0 g (0.020 mol) of (S)-9-oxo-12,12a-dihydro-9H,11H-azeto[2,1-c]imidazo[1,5-a][1,4] benzodiazepine-1-carbonitrile in 100 ml of pyridine and 1 ml of triethylamine. The dark brown solution was left to stand for 70 hrs., then degassed with a stream of nitrogen and subsequently completely freed from the solvents. The residue was partitioned between dichloromethane and water and extracted. The pale yellow product was chromatographed over silica gel with ethyl acetate as the eluent, stirred vigorously in ether for 16 hrs. and subsequently filtered off under suction. There were obtained 3.8 g (67%) of (S)-9-oxo-12,12a-dihydro-9H,11H-azeto[2,1-c]imidazo-[1,5-a][1,4]benzodiazepine-1-thiocarboxamide as pale yellow crystals; m.p. 227°–230° and $[\alpha]_D^{20}$=−473.7° (DMF, c=1%).

d) A yellow suspension of 4.86 g (0.0171 mol) of (S)-9-oxo-12,12a-dihydro-9H,11H-azeto[2,1-c]imidazo[l,5-a][1,4]benzodiazepine-1-thiocarboxamide in 120 ml of dioxan was treated with 2.38 g (0.0188 mol) of 1,3-dichloro-2-propanone. The suspension was boiled at reflux for 48 hrs. The solution obtained was cooled and completely freed from the solvents. The product was chromatographed over silica gel with dichloromethane/ethyl acetate 1:1 as the eluent and recrystallized from hot ethyl acetate. There were obtained 2.54 g (42%) of (S)-1-(4-chloromethyl-thiazol-2-yl)-12,12a-dihydro-9H,11H-azeto[2,1-c]-imidazo[1,5-a][1,4] benzodiazepin-9-one as white crystals; m.p. 248°–249° and $[\alpha]_D^{20}$=−186.1° (DMF, c=1%).

A further 1.8 g (30%) of pure product were obtained from the mother liquor after vigorous stirring in ether.

e) A solution of 1.0 g (0.0028 mol) of (S)-1-(4-chloromethyl-thiazol-2-yl)-12,12a-dihydro-9H,11H-azeto [2,1-c]imidazo[1,5-a][1,4]benzodiazepin-9-one in 50 ml of tetrahydrofuran was treated with 4.6 ml (0.034 mol) of dipropylamine. After stirring at reflux for 16 hrs. the solution obtained was completely freed from the solvents. The residue was chromatographed over silica gel with ethyl acetate/tetrahydrofuran 2:1 as the eluent. There were obtained 1.04 g (95%) of (S)-1-(4-dipropylaminomethyl-thiazol-2-yl)-12,12a-dihydro-9H,11H-azeto[2,1-c]imidazo[1,5-a][1,4] benzodiazepin-9-one as a pale yellow oil; $[\alpha]_D^{20}$=−253.8° (MeOH, c=1%).

MS: m/e (% basic peak)=421 ($C_{23}H_{27}N_5OS+$, 2), 392 (22), 322 (100), 321 (90), 293 (18), 265 (16), 223 (9.5), 196 (13), 100 (90), 71 (34)

f) 0.97 g (0.0023 mol) of (S)-1-(4-dipropylaminomethyl-thiazol-2-yl)-12,12a-dihydro-9H,11H-azeto[2,1-c]imidazo [1,5-a][1,4]benzodiazepin-9-one in 30 ml of ethanol was treated with 0.48 ml (0.0023 mol) of 4.78N ethanolic hydrochloric acid. After stirring at room temperature for 10 minutes the solution obtained was completely freed from the solvents. The residue was recrystallized from ethanol/ether. There was obtained 0.77 g (82%) of (S)-1-(4-dipropylaminomethyl-thiazol-2-yl)-12,12a-dihydro-9H, 11H-azeto[2,1-c]imidazo[1,5-a][1,4]benzodiazepin-9-one hydrochloride (1:1) as white crystals; m.p. 225°–228° and $[\alpha]_D^{20}$=–306.1° (MeOH, c=1%).

EXAMPLE 19 a) A stream of hydrogen sulphide was conducted for 1 hr. through a solution of 9.64 g (0.354 mol) of 7-chloro-5-methyl-6-oxo-5,6-dihydro-4H-imidazo[1,5-a][1,4] benzodiazepine-3-carbonitrile in 210 ml of pyridine and 2.1 ml of triethylamine. The green solution was left to stand for 64 hrs., then de-gassed with a stream of nitrogen and subsequently completely freed from the solvents. The solid residue was partitioned between dichloromethane and water and the suspension obtained was suction filtered. There were obtained 9.41 g (87%) of 7-chloro-5-methyl-6-oxo-5,6-dihydro-4H-imidazo[1,5-a][1,4]benzodiazepine-3-thiocarboxamide as yellow crystals. An analytical sample was obtained from the organic phase after recrystallization in methanol. Yellow crystals; m.p. 300°–302°.

b) A yellow suspension of 10.3 g (0.0336 mol) of 7-chloro-5-methyl-6-oxo-5,6-dihydro-4H-imidazo[1,5-a][1,4]benzodiazepine-3-thiocarboxamide in 220 ml of dioxan was treated with 4.69 g (0.0370 mol) of 1,3-dichloro-2-propanone. The solution was boiled at reflux for 16 hrs., cooled and suction filtered. There were obtained 11.1 g (87%) of 7-chloro-3-(4-chloromethyl-thiazol-2-yl)-5-methyl-5,6-dihydro-4H-imidazo[1,5-a][1,4]benzodiazepin-6-one as brown crystals. An analytical sample was recrystallized from hot acetonitrile. White crystals; m.p. 277°–279°.

c) A suspension of 1.0 g (0.00263 mol) of 7-chloro-3-(4-chloromethyl-thiazol-2-yl)-5-methyl-5,6-dihydro-4H-imidazo-[1,5-a][1,4]benzodiazepin-6-one in 60 ml of tetrahydrofuran was treated with 7.2 ml (0.0527 mol) of dipropylamine and 5 ml of dimethylformamide. After stirring at reflux for 16 hrs. the suspension obtained was filtered and the solution was completely freed from the solvents. The residue was chromatographed over silica gel with ethyl acetate as the eluent and recrystallized from hot isopropyl ether. There was obtained 0.52 g (44%) of 7-chloro-3-(4-dipropylaminomethyl-thiazol-2-yl)-5-methyl-5,6-dihydro-4H-imidazo[1,5-a][1,4]benzodiazepin-6-one as white crystals; m.p. 121°–123°.

d) 0.86 g (0.00193 mol) of 7-chloro-3-(4-dipropylaminomethyl-thiazol-2-yl)-5-methyl-5,6-dihydro-4H-imidazo[1,5-a][1,4]benzodiazepin-6-one in 25 ml of ethanol was treated with 0.52 ml (0.00192 mol) of 3.7N ethanolic hydrochloric acid. After stirring at room temperature for 10 minutes the solution obtained was completely freed from the solvents. The residue was recrystallized from ethanol/ether. There was obtained 0.83 g (89%) of 7-chloro-3-(4-dipropylaminomethyl-thiazol-2-yl)-5-methyl-5,6-dihydro-4H-imidazo[1,5-a][1,4]benzodiazepin-6-one hydrochloride (1:1) as white crystals; m.p. 227°–229°.

EXAMPLE 20 a) A suspension of 11.9 g (0.0394 mol) of (S)-8-chloro-9-oxo-12,12a-dihydro-9H,11H-azeto[2,1-c]imidazo[1,5-a] [1,4]benzodiazepine-1-carboxamide in a mixture of 85 ml of dioxan and 6.8 ml of pyridine was treated dropwise at 0° with 7.1 ml (0.051 mol) of trifluoroacetic anhydride. The suspension was stirred at 50° for 3 hrs., cooled and poured on to ice-water. After stirring for 1½ hr. the suspension was suction filtered. There were obtained 11.2 g (100%) of (S)-8-chloro-9-oxo-12,12a-dihydro-9H,11H-azeto[2,1-c] imidazo[1,5-a][1,4]benzodiazepine-1-carbonitrile as white crystals; m.p. 130° (dec.).

b) A stream of hydrogen sulphide was conducted for 1 hr. through a solution of 11.3 g (0.0396 mol) of (S)-8-chloro-9-oxo-12,12a-dihydro-9H,11 H-azeto[2,1-c]imidazo[1,5-a] [1,4]benzodiazepine-1-carbonitrile in 230 ml of pyridine and 2.3 ml of triethylamine. The green solution was left to stand for 48 hrs., then de-gassed with a stream of nitrogen and subsequently completely freed from the solvents. The residue was partitioned between dichloromethane and water and extracted. The pale yellow product was recrystallized in tetrahydrofuran and subsequently in methanol. There were obtained 4.44 g (35%) of (S)-8-chloro-9-oxo-12,12a-dihydro-9H,11H-azeto[2,1-c]imidazo[1,5-a][1,4] benzodiazepine-1-thiocarboxamide as pale yellow crystals; m.p. 250°–253° and $[\alpha]_D^{20}$=–330.6° (DMF, c=1%).

c) A yellow suspension of 7.91 g (0.0248 mol) of (S)-8-chloro-9-oxo-12,12a-dihydro-9H,11H-azeto[2,1-c]imidazo [1,5-a][1,4]-benzodiazepine-1-thiocarboxamide in 160 ml of dioxan was treated with 3.46 g (0.0273 mol) of 1,3-dichloro-2-propanone. The suspension was boiled at reflux for 24 hrs. The suspension obtained was cooled and filtered. The solution was completely freed from the solvents. The crude product was chromatographed over silica gel with cyclohexane/ethyl acetate 1:2 as the eluent and recrystallized from hot acetonitrile. There was obtained 0.85 g (8.7%) of (S)-8-chloro-1-(4-chloromethyl-thiazol-2-yl)-12, 12a-dihydro-9H,11H-azeto[2,1-c]imidazo[1,5-a][1,4] benzodiazepin-9-one as white crystals; m.p. 221–223 and $[\alpha]_D^{20}$=–163.0° (MeOH, c=1%).

d) A solution of 1.1 g (0.00281 mol) of (S)-8-chloro-1-(4-chloromethyl-thiazol-2-yl)-12,12a-dihydro-9H,11H-azeto[2,1-c]imidazo[1,5-a][1,4]benzodiazepin-9-one in 70 ml of tetrahydrofuran was treated with 7.7 ml (0.0562 mol) of dipropylamine. After stirring at reflux for 16 hrs. the solution obtained was completely freed from the solvents. The residue was chromatographed over silica gel with ethyl acetate as the eluent and recrystallized from ethyl acetate/ ether. There was obtained 0.82 g (64%) of (S)-8-chloro-1-(4-dipropylaminomethyl-thiazol-2-yl)-12,12a-dihydro-9H, 11H-azeto[2,1-c]imidazo[1,5-a][1,4]-benzodiazepin-9-one as white crystals; m.p. 200°–201° and $[\alpha]_D^{20}$=–181.2° ($CHCl_3$, c=1%).

e) 0.91 g (0.0020 mol) of (S)-8-chloro-1-(4-dipropylaminomethyl-thiazol-2-yl)-12,12a-dihydro-9H, 11H-azeto[2,1-c]-imidazo[1,5-a][1,4]benzodiazepin-9-one in 30 ml of dichloromethane was treated with 0.54 ml (0.0020 mol) of 3.7N ethanolic hydrochloric acid. After stirring at room temperature for 10 minutes the solution was completely freed from the solvents. The residue was recrystallized from ethanol/ether. There was obtained 0.85 g (87%) of (S)-8-chloro-1-(4-dipropylaminomethyl-thiazol-2-yl)-12, 12a-dihydro-9H,11H-azeto[2,1-c]imidazo[1,5-a][1,4] benzodiazepin-9-one hydrochloride (1:1) as white crystals; m.p. 221°–223° and $[\alpha]_D^{20}$=–245.7° (MeOH, c=1%).

EXAMPLE 21 a) A suspension of 6.8 g (0.0204 mol) of (S)-8-chloro-9-oxo-11,12,13,13a-tetrahydro-9H-imidazo[1,5-a]pyrrolo[2, 1-c][1,4]-benzodiazepine-thiocarboxamide in 100 ml of dioxan was treated with 2.85 g (0.0224 mol) of 1,3-dichloro-2-propanone and boiled at reflux for 48 hrs. After cooling 30 g of silica gel were added and the mixture was stirred for a further 1 hr. The mixture was concentrated in a water-jet vacuum and dried in a high vacuum. The crude product, adsorbed on silica gel, was applied to a silica gel column equilibrated with ethyl acetate and then eluted with ethyl acetate. There were obtained 4.7 g (58%) of (S)-8-chloro-1-(4-chloromethyl-thiazol-2-yl)-11,12,13,13a-tetrahydro-9H-imidazo[1,5-a]pyrrolo[2,1-c][1,4]benzodiazepin-9-one in the form of white crystals.

MS: m/e (% basic peak)=404 ($C_{18}H_{14}Cl_2N_4OS+$, 60), 375 (100), 71 (45), 45 (50)

b) A solution of 1.0 g (0.0025 mol) of (S)-8-chloro-1-(4-chloromethyl-thiazol-2-yl)-11,12,13,13a-tetrahydro-9H-imidazo[1,5-a]pyrrolo[2,1-c][1,4]benzodiazepin-9-one in 20 ml of tetrahydrofuran was added dropwise within ½ hr. to 20 ml of a dimethylamine-saturated tetrahydrofuran solution. Subsequently, the mixture was stirred at room temperature for 36 hrs. Then, all volatiles were removed in a water-jet vacuum and the residue was crystallized from ethyl acetate.

The colorless crystal slurry (0.546 g; 54%) was suspended in 15 ml of diethyl ether and treated with sufficient methanol to form a clear solution. After the addition of 1.4 ml of 0.83M (0.0011 mol) methanolic hydrochloric acid there crystallized slowly 0.326 g (60%) of (S)-8-chloro-1-(4-dimethylaminomethyl-thiazol-2-yl)-11,12,13,13a-tetrahydro-9H-imidazo[1,5-a]pyrrolo[2,1-c][1,4]benzodiazepin-9-one hydrochloride (1:1) in the form of white crystals; m.p. >280° and $[\alpha]_D^{20}$=−93.9° (MeOH, c=1%).

MS: m/e (% basic peak)=413 ($C_{20}H_{20}ClN_5OS+$, 7), 370 (100), 301 (10), 44 (9)

EXAMPLE 22 a) A solution of 1.0 g (0.0025 mol) of (S)-8-chloro-1-(4-chloromethyl-thiazol-2-yl)-11,12,13,13a-tetrahydro-9H-imidazo[1,5-a]pyrrolo[2,1-c][1,4]benzodiazepin-9-one in 20 ml of tetrahydrofuran was treated with 5 ml (0.037 mol) of dipropylamine and stirred at 50° for 96 hrs. All volatiles were removed in a water-jet vacuum and the residue was taken up with ethyl acetate and water. The organic phase was dried over magnesium sulphate, concentrated and the residue remaining was chromatographed over silica gel with methylene chloride/methanol 95:5 as the eluent. After recrystallization from ethyl acetate there was obtained 0.67 g (58%) of (S)-8-chloro-1-(4-dipropylaminomethyl-thiazol-2-yl)-11,12,13,13a-tetrahydro-9H-imidazo-[1,5-a]pyrrolo[2,1-c][1,4]benzodiazepin-9-one in the form of white crystals; m.p. 213°–214° and $[\alpha]_D^{20}$=−68.5° (MeOH, c=0.8%).

b) 0.51 g (0.0011 mol) of (S)-8-chloro-1-(4-dipropylaminomethyl-thiazol-2-yl)-11,12,13,13a-tetrahydro-9H-imidazo[1,5-a]pyrrolo[2,1-c][1,4]benzodiazepin-9-one was suspended in 10 ml of water and treated with 10.3 ml of 0.1N (0.0010 mol) aqueous hydrochloric acid. After stirring at room temperature for 1 hr. the mixture was filtered and the filtrate was lyophilized. There was obtained 0.50 g (90%) of (S)-8-chloro-1-(4-dipropylaminomethyl-thiazol-2-yl)-11,12,13,13a-tetrahydro-9H-imidazo[1,5-a]pyrrolo[2,1-c][1,4]benzodiazepin-9-one hydrochloride (1:1).

MS: m/e (% basic peak)=469 ($C_{24}H_{28}ClN_5OS+$, 1), 440 (19), 370 (74), 100 (100).

EXAMPLE 23 a) A solution of 1.3 g (0.0032 mol) of (S)-8-chloro-1-(4-chloromethyl-thiazol-2-yl)-11,12,13,13a-tetrahydro-9H-imidazo[1,5-a]pyrrolo[2,1-c][1,4]benzodiazepin-9-one in 15 ml of tetrahydrofuran was treated with 4 ml (0.048 mol) of pyrrolidine and stirred at 50° for 96 hrs. All volatiles were removed in a water-jet vacuum and the residue was taken up with ethyl acetate and water. The organic phase was dried over magnesium sulphate, concentrated and the residue remaining was chromatographed over silica gel with methylene chloride/methanol 95:5 as the eluent. After recrystallization from ethyl acetate there was obtained 0.62 g (44%) of (S)-8-chloro-1-(4-pyrrolidin-1-ylmethyl-thiazol-2-yl)-11,12,13,13a-tetrahydro-9H-imidazo-[1,5-a]pyrrolo[2,1-c][1,4]benzodiazepin-9-one in the form of white crystals; m.p. 213°–214° and $[\alpha]_D^{20}$=−71.2° (MeOH, c=1%).

b) 0.56 g (0.0012 mol) (S)-8-chloro-1-(4-pyrrolidin-1-ylmethyl-thiazol-2-yl)-11,12,13,13a-tetrahydro-9H-imidazo-[1,5-a]pyrrolo[2,1-c][1,4]benzodiazepin-9-one was suspended in 10 ml of water and treated with 12 ml of 0.1N (0.0012 mol) aqueous hydrochloric acid. After stirring at room temperature for 1 hr. the mixture was filtered and the filtrate was lyophilized. There was obtained 0.57 g (93%) of (S)-8-chloro-1-(4-pyrrolidin-1-ylmethyl-thiazol-2-yl)-11,12,13,13a-tetrahydro-9H-imidazo[1,5-a]pyrrolo[2,1-c][1,4]benzodiazepin-9-one hydrochloride (1:1).

MS: m/e (% basic peak)=439 ($C_{22}H_{22}ClN_5OS+$, 1), 370 (100), 301 (9), 70 (33).

EXAMPLE 24 a) A solution of 0.81 g (0.002 mol) of (S)-8-chloro-1-(4-chloromethyl-thiazol-2-yl)-11,12,13,13a-tetrahydro-9H-imidazo[1,5-a]pyrrolo[2,1-c][1,4]benzodiazepin-9-one in 5 ml of tetrahydrofuran was treated with 3 ml (0.024 mol) of diallylamine and stirred at 50° for 8 hrs. All volatiles were removed in a water-jet vacuum and the residue was chromatographed over silica gel with methylene chloride/methanol 98:2 as the eluent. After recrystallization from diethyl ether there was obtained 0.52 g (55%) of (S)-8-chloro-1-(4-diallylaminomethyl-thiazol-2-yl)-11,12,13,13a-tetrahydro-9H-imidazo[1,5-a]pyrrolo[2,1-c][1,4]benzodiazepin-9-one in the form of white crystals; m.p. 186°–187° and $[\alpha]_D^{20}$=−67.5° (MeOH, c=1%).

b) 0.50 g (0.0011 mol) of (S)-8-chloro-1-(4-diallylaminomethyl-thiazol-2-yl)-11,12,13,13a-tetrahydro-9H-imidazo[1,5-a]pyrrolo[2,1-c][1,4]benzodiazepin-9-one was suspended in 10 ml of water and treated with 10.6 ml of 0.1N (0.00106 mol) aqueous hydrochloric acid. After stirring at room temperature for 1 hr. the mixture was filtered and the filtrate was lyophilized. There was obtained 0.50 g (95%) of (S)-8-chloro-1-(4-diallylaminomethyl-thiazol-2-yl)-11,12,13,13a-tetrahydro-9H-imidazo[1,5-a]pyrrolo[2,1-c][1,4]benzodiazepin-9-one hydrochloride (1:1).

MS: m/e (% basic peak)=465 ($C_{24}H_{24}ClN_5OS+$, 11), 370 (100), 341 (14), 301 (14), 96 (65).

EXAMPLE 25 a) A stream of hydrogen sulphide was conducted for ½ hr. through a solution of 4.4 g (0.0172 mol) of 8-fluoro-5-methyl-6-oxo-5,6-dihydro-4H-imidazo[1,5-a][1,4]benzodiazepine-3-carbonitrile in 100 ml of pyridine and 1 ml of triethylamine. The dark green solution was left to stand for 64 hrs., then de-gassed with a stream of nitrogen and subsequently completely freed from the solvents. The residue was partitioned between dichloromethane/tetrahydrofuran and water, extracted, concentrated, stirred vigorously in ether and filtered off under suction. There were obtained 4.55 g (91%) of 8-fluoro-5-methyl-6-oxo-5,6-dihydro-4H-imidazo[1,5-a][1,4]benzodiazepine-3-thiocarboxamide as yellow crystals.

An analytical sample was chromatographed on silica gel with dichloromethane/methanol 19:1 as the eluent, recrystallized from methanol and gave beige crystals; m.p. 280°–282° (dec.).

b) A suspension of 4.51 g (0.0155 mol) of 8-fluoro-5-methyl-6-oxo-5,6-dihydro-4H-imidazo[1,5-a][1,4]benzodiazepine-3-thiocarboxamide in 100 ml of dioxan was treated with 2.16 g (0.0171 mol) of 1,3-dichloro-2-propanone, The suspension was boiled at reflux for 41 hrs., cooled and completely freed from the solvents. The residue was chromatographed over silica gel with dichloromethane/ethyl acetate 1:1 as the eluent and recrystallized from hot ethyl acetate. There were obtained 3.23 g (57%) of 3-(4-chloromethyl-thiazol-2-yl)-8-fluoro-5-methyl-5,6-dihydro-4H-imidazo[1,5-a][1,4]benzodiazepin-6-one as white crystals; m.p. 239°–241°.

A further 1.65 g (29%) of pure product were obtained from the mother liquor after vigorous stirring in ether.

c) A suspension of 1.0 g (0.00275 mol) of 3-(4-chloromethylthiazol-2-yl)-8-fluoro-5-methyl-5,6-dihydro-4H-imidazo[1,5-a][1,4]benzodiazepin-6-one in 50 ml of tetrahydrofuran was treated with 4.5 ml (0.033 mol) of dipropylamine. After stirring at 50° for 12 hrs. the solution obtained was completely freed from the solvents. The residue was chromatographed over silica gel with dichloromethane/methanol 19:1 as the eluent and recrystallized from hot isopropyl ether. There was obtained 0.34 g (29%) of 3-(4-dipropylaminomethyl-thiazol-2-yl)-8-fluoro-5-methyl-5,6-dihydro-4H-imidazo[1,5-a][1,4]benzodiazepin-6-one as white crystals; m.p.134°–136°.

d) 0.85 g (0.0020 mol) of 3-(4-dipropylaminomethyl-thiazol-2-yl)-8-fluoro-5-methyl-5,6-dihydro-4H-imidazo[1,5-a][1,4]-benzodiazepin-6-one in 30 ml of ethanol was treated with 0.42 ml (0.0020 mol) of 4.78N ethanolic hydrochloric acid. After stirring at room temperature for 10 minutes the solution obtained was completely freed from the solvents. The residue was recrystallized from ethanol/ether. There was obtained 0.58 g (63%) of 3-(4-dipropylaminomethyl-thiazol-2-yl)-8-fluoro-5-methyl-5,6-dihydro-4H-imidazo[1,5-a][1,4]benzodiazepin-6-one hydrochloride (1:1) as white crystals; m.p. 206°–210°.

EXAMPLE 26 a) A suspension of 1.0 g (0.00275 mol) of 3-(4-chloromethylthiazol-2-yl)-8-fluoro-5-methyl-5,6-dihydro-4H-imidazo[1,5-a][1,4]benzodiazepin-6-one in 50 ml of tetrahydrofuran was treated with 4.1 ml (0.033 mol) of diallylamine. After stirring at reflux for 18 hrs. the solution obtained was completely freed from the solvents. The residue was chromatographed over silica gel with dichloromethane/methanol 19:1 as the eluent and recrystallized from hot isopropyl ether. There was obtained 0.76 g (66%) of 3-(4-diallylaminomethyl-thiazol-2-yl)-8-fluoro-5-methyl-5,6-dihydro-4H-imidazo[1,5-a][1,4]benzodiazepin-6-one as white crystals; m.p. 125°–127°.

b) 0.90 g (0.00212 mol) of 3-(4-diallylaminomethyl-thiazol-2-yl)-8-fluoro-5-methyl-5,6-dihydro-4H-imidazo[1,5-a][1,4]-benzodiazepin-6-one in 40 ml of ethanol was treated with 0.45 ml (0.00215 mol) of 4.78N ethanolic hydrochloric acid. After stirring at room temperature for 15 minutes the solution obtained was completely freed from the solvents. The residue was recrystallized from ethanol/ether. There was obtained 0.78 g (80%) of 3-(4-diallylaminomethyl-thiazol-2-yl)-8-fluoro-5-methyl-5,6-dihydro-4H-imidazo[1,5-a][1,4]benzodiazepin-6-one hydrochloride (1:1) as white crystals; m.p. 152°–155°.

EXAMPLE 27 a) A suspension of 19.8 g (0.0639 mol) of 7-chloro-8-fluoro-5-methyl-6-oxo-5,6-dihydro-4H-imidazo[1,5-a][1,4]benzodiazepine-3-carboxylic acid in 100 ml of dimethylformamide was treated portionwise with 10.9 g (0.0671 mol) of carbonyldiimidazole while gassing with argon. After completion of the $CO_2$ evolution the yellow solution obtained was stirred at 50° for ½ hr. After cooling to room temperature it was treated dropwise with 20 ml of 25 percent aqueous ammonia solution and stirred at room temperature for ¼ hr. The brownish solution was poured on to 600 ml of ice-water. After vigorous stirring the suspension obtained was suction filtered. There were obtained 14.4 g (73%) of 7-chloro-8-fluoro-5-methyl-6-oxo-5,6-dihydro-4H-imidazo[1,5-a][1,4]benzodiazepine-3-carboxamide as beige crystals; m.p. 292°–294°.

b) A suspension of 14.4 g (0.0466 mol) of 7-chloro-8-fluoro-5-methyl-6-oxo-5,6-dihydro-4H-imidazo[1,5-a][1,4]benzodiazepin-3-carboxamide in a mixture of 60 ml of dioxan and 8 ml of pyridine was treated dropwise at 0° with 6.8 ml (0.049 mol) of trifluoroacetic anhydride. The dark solution was stirred at 50° for 3 hrs., cooled, poured on to 400 ml of icewater, treated with ethyl acetate and extracted. The organic solution was filtered on 100 g of silica gel and rinsed with 200 ml of ethyl acetate. The product was recrystallized from m hot ethyl acetate. There were obtained 12 g (89%) of 7-chloro-8-fluoro-5-methyl-6-oxo-5,6-dihydro-4H-imidazo[1,5-a][1,4]-benzodiazepine-3-carbonitrile as light yellowish crystals; m.p. 221°–223°.

c) A stream of hydrogen sulphide was conducted for ½ hr. through a solution of 3.0 g (0.0103 mol) of 7-chloro-8-fluoro-5-methyl-6-oxo-5,6-dihydro-4H-imidazo[1,5-a][1,4]benzodiazepine-3-carbonitrile in 10 ml of pyridine and 1.0 ml of triethylamine. The green solution was left to stand for 64 hrs., then degassed with a stream of nitrogen and subsequently completely freed from the solvents. The residue was partitioned between dichloromethane and water and the suspension obtained was suction filtered. There were obtained 2.45 g (73%) of 7-chloro-8-fluoro-5-methyl-6-oxo-5,6-dihydro-4H-imidazo[1,5-a][1,4]-benzodiazepine-3-thiocarboxamide.

An analytical sample (0.66 g, 20%) was obtained after extracting the liquid phases, stirring the residue vigorously in ether and recrystallizing the solid from hot methanol. Beige crystals; m.p. 204°–306°.

d) A yellow suspension of 2.45 g (0.00754 mol) of 7-chloro-8-fluoro-5-methyl-6-oxo-5,6-dihydro-4H-imidazo[1,5-a][1,4]-benzodiazepine-3-thiocarboxamide in 130 ml of dioxan was treated with 1.05 g (0.00829 mol) of 1,3-dichloro-2-propanone. The suspension was boiled at reflux for 20 hrs. and cooled. A further 1.05 g (0.00829 mol) of 1,3-dichloro-2-propanone and 60 ml of dioxan were added and the solution was boiled at reflux for a further 16 hrs. The solution was cooled and completely freed from the solvents. The residue was chromatographed over silica gel with cyclohexane/ethyl acetate 1:2 as the eluent and recrystallized from hot acetonitrile. There were obtained 1.05 g (35%) of 7-chloro-3-(4-chloromethyl-thiazol-2-yl)-8-fluoro-5-methyl-5,6-dihydro-4H-imidazo[1,5-a][1,4]benzodiazepin-6-one as white crystals; m.p. 234°–235°.

e) A suspension of 1.11 g (0.0028 mol) of 7-chloro-3-(4-chloromethyl-thiazol-2-yl)-8-fluoro-5-methyl-5,6-dihydro-4H-imidazo[1,5-a][1,4]benzodiazepin-6-one in 80 ml of tetrahydrofuran was treated with 7.6 ml (0.056 mol) of dipropylamine. After stirring at reflux for 24 hrs. the solution obtained was completely freed from the solvents. The residue was chromatographed over silica gel with acetonitrile as the eluent and recrystallized from hot isopropyl ether. There was obtained 0.50 g (39%) of 7-chloro-3-(4-dipropylaminomethyl-thiazol-2-yl)-8-fluoro-5-methyl-5,6-dihydro-4H-imidazo[1,5-a][1,4]-benzodiazepin-6-one as white crystals; m.p. 123°–1250.

f) 0.87 g (0.00188 mol) of 7-chloro-3-(4-dipropylaminomethyl-thiazol-2-yl)-8-fluoro-5-methyl-5,6-dihydro-4H-imidazo[1,5-a][1,4]benzodiazepin-6-one in 20 ml of ethanol was treated with 0.51 ml (0.00189 mol) of 3.7N ethanolic hydrochloric acid. After stirring at room temperature for 10 minutes the solution obtained was completely freed from the solvents. The residue was recrystallized from ethanol/ether. There was obtained 0.89 g (95%) of 7-chloro-3-(4-dipropylaminomethyl-thiaozl- 2-yl)-8-fluoro-5-methyl-5,6-dihydro-4H-imidazo[1,5-a][1,4]benzodiazepin-6-one hydrochloride (1:1) as white crystals; m.p. 216°–218°.

EXAMPLE 28 a) A suspension of 11.3 g (0.0437 mol) of 5-methyl-6-oxo-5,6-dihydro-4H-imidazo[1,5-a][1,4]benzodiazepine-3-carboxylic acid in 220 ml of dimethylformamide was treated portionwise with 7.80 g (0.048 mol) of carbonyldiimidazole while gassing with argon. After completion of the $CO_2$ evolution the mixture was stirred at 55° for 2 hrs. After cooling to 0°–5° the pale yellow solution obtained was treated with 7.48 g (0.0532 mol) of L-serine methyl ester hydrochloride and with 6.7 ml (0.048 mol) of triethylamine and stirred at room temperature for 70 hrs. The light suspension was completely freed from the solvents. The residue was dissolved in hot water and extracted continuously with ethyl acetate. The yellow oily residue was chromatographed over silica gel with ethyl acetate as the eluent. There were obtained 10.7 g (68%) of methyl (S)-3-hydroxy-2-(5-methyl-6-oxo-5,6-dihydro-4H-imidazo[1,5-a][1,4]benzodiazepin-3-ylcarbonylamino)-propionate as a white solid. An analytical sample was recrystallized from ethyl acetate/diethyl ether and gave white crystals; m.p. 180°–181°. $[\alpha]_D^{20}$=+12.9° ($CHCl_3$, c=1%).

b) A solution of 10.0 g (0.0279 mol) of methyl (S)-3-hydroxy-2-(5-methyl-6-oxo-5,6-dihydro-4H-imidazo[1,5-a][1,4]benzodiazepin-3-ylcarbonylamino)-propionate in 500 ml of tetrahydrofuran was treated while gassing with argon with 7.25 g (0.0304 mol) of methoxycarbonylsulphamoyl-triethylammonium hydroxide internal salt (Burgess reagent) according to the method described in Tert. Letters 1992, 33, 907. The mixture was boiled at reflux for 1 hr. and completely freed from the solvents. The residue was dissolved in dichloromethane and chromatographed over silica gel with ethyl acetate/ethanol 9:1 as the eluent. There were obtained 4.4 g (46%) of methyl (S)-2-(5-methyl-6-oxo-5,6-dihydro-4H-imidazo[1,5-a][1,4]benzodiazepin-3-yl)-4,5-dihydro-oxazole-4-carboxylate as a white solid. An analytical sample was recrystallized from ethanol/diethyl ether and gave white crystals; m.p. 190°–192°. $[\alpha]_D^{20}$=+45.4° ($CHCl_3$, c=1%).

c) A solution of 4.34 g (0.0128 mol) of methyl (S)-2-(5-methyl-6-oxo-5,6-dihydro-4H-imidazo[1,5-a][1,4]benzodiazepin-3-yl)-4,5-dihydro-oxazole-4-carboxylate in 160 ml of hot benzene was treated with 2.02 g (0.0141 mol) of copper bromide and 3.75 ml (0.020 mol) of tert-butyl perbenzoate according to the method described in Tert. Letters 1994, 35, 2481. The mixture was boiled at reflux for 1 hr., cooled and treated with 100 ml of water. The mixture was filtered, extracted with benzene and chromatographed over silica gel with ethyl acetate as the eluent. There were obtained 1.36 g (32%) of methyl 2-(5-methyl-6-oxo-5,6-dihydro-4H-imidazo[1,5-a][1,4]-i5 benzodiazepin-3-yl)-oxazole-4-carboxylate as a white solid. An analytical sample was recrystallized from hot methanol and gave white crystals; m.p. 264°–265°.

d) 1.2 g (0.0035 mol) of methyl 2-(5-methyl-6-oxo-5,6-2 dihydro-4H-imidazo[1,5-a][1,4]benzodiazepin-3-yl)-oxazole-4-carboxylate were dissolved in 700 ml of hot tetrahydrofuran and cooled to −78°. The solution was treated dropwise with 10.5 ml (0.0105 mol) of a 1M lithium aluminum hydride solution in tetrahydrofuran and stirred at −78° for 20 hrs. 100 ml of ethyl acetate were added dropwise at −50° and 12 ml of saturated sodium sulphate solution were added dropwise at 0°. The suspension was dried with sodium sulphate, suction filtered and the filtrate was completely freed from the solvents.

The crude product was dissolved in 140 ml of dichloromethane. The solution was stirred at room temperature with 1.3 ml (0.01 8 mol) of thionyl chloride and stirred for 1 hr. The solution was treated with saturated sodium bicarbonate solution, extracted and chromatographed over silica gel with ethyl acetate as the eluent. There was obtained 0.74 g (64%) of 3-(4-chloromethyl-oxazol-2-yl)-5-methyl-5,6-dihydro-4H-imidazo[1,5-a][1,4]benzodiazepin-6-one as a white solid. An analytical sample was recrystallized from hot acetonitrile and gave white crystals; m.p. 196°–198°.

e) 0.30 g (0.00091 mol) of 3-(4-chloromethyl-oxazol-2-yl)-5-methyl-5,6-dihydro-4H-imidazo[1,5-a][1,4]benzodiazepin-6-one was dissolved in 40 ml of tetrahydrofuran, treated with 2.5 ml (0.0183 mol) of dipropylamine and boiled at reflux for 20 hrs. The solution was completely freed from the solvents and the residue was chromatographed over silica gel with ethyl acetate/ethanol 9:1 as the eluent. There was obtained 0.24 g (67%) of 3-(4-dipropylaminomethyl-oxazol-2-yl)-5-methyl-5,6-dihydro-4H-imidazo[1,5-a][1,4]benzodiazepin-6-one as a white solid. An analytical sample was recrystallized from diisopropyl ether and gave white crystals; m.p. 109°–110°.

f) 0.24 g (0.00061 mol) of 3-(4-dipropylaminomethyl-oxazol-2-yl)-5-methyl-5,6-dihydro-4H-imidazo[1,5-a][1,4]benzodiazepin-6-one was dissolved in 30 ml of ethanol and treated with 0.1 6 ml (0.00061 mol) of 3.7N ethanolic hydrochloric acid. The solution was completely freed from the solvents and recrystallized from ethanol/diethyl ether. There was obtained 0.22 g (84%) of 3-(4-dipropylaminomethyl-oxazol-2-yl)-5-methyl-5,6-dihydro-4H-imidazo[1,5-a][1,4]benzodiazepin-6-one hydrochloride as white crystals; m.p. 203°–205°.

EXAMPLE 29 a) A suspension of 14.1 g (0.0484 mol) of 7-chloro-5-methyl-6-oxo-5,6-dihydro-4H-imidazo[1,5-a][1,4]benzodiazepine-3-carboxylic acid in 150 ml of dimethylformamide was treated portionwise with 8.24 g (0.0508 mol). of carbonyldiimidazole while gassing with argon. After completion of the $CO_2$ evolution the mixture was stirred at 65° for 3 hrs. After cooling to 0°–5° the white suspension obtained was treated with 8.28 g (0.0532 mol) of L-serine methyl ester hydrochloride and with 7.452 ml (0.0532 mol) of triethylamine and stirred at room temperature for 21 hrs. The white suspension was suction filtered and the filtrate was completely freed from the solvents. The orange oily residue was partitioned between ethyl acetate and water, extracted, chromatographed over silica gel with ethyl acetate/ethanol 9:1 as the eluent and recrystallized from hot ethyl acetate; the mother liquor was then digested with diethyl ether. There were obtained a total of 14.0 g (74%) of methyl (S)-2-(7-chloro-5-methyl-6-oxo-5,6-dihydro-4H-imidazo[1,5-a]1,4]-benzodiazepin-3-ylcarbonylamino)-3-hydroxy-propionate as white crystals; m.p. 178°–180°. $[\alpha]_D^{20}$=+1.2° (CH$_2$Cl$_2$, c=1%).

b) A solution of 14.0 g (0.0356 mol) of methyl (S)-2-(7-chloro-5-methyl-6-oxo-5,6-dihydro-4H-imidazo[1,5-a][1,4]-benzodiazepin-3-ylcarbonylamino)-3-hydroxy-propionate in 250 ml of tetrahydrofuran was treated while gassing with argon with 9.3 g (0.0392 mol) of methoxycarbonylsulphamoyl-triethylammonium hydroxide internal salt (Burgess reagent) according to the method described in Tert. Letters 1992, 33, 907. The mixture was boiled at reflux for 3 ½ hrs. and completely freed from the solvents. The residue was partitioned between dichloromethane and water, extracted and chromatographed over silica gel with ethyl acetate/ethanol 19:1 as the eluent. There were obtained 6.80 g (51%) of methyl (S)-2-(7-chloro-5-methyl-6-oxo-5,6-dihydro-4H-imidazo[1,5-a][1,4]benzodiazepin-3-yl)-4,5-dihydrooxazole-4-carboxylate as white crystals; m.p. 216°–218°.

c) A solution of 6.80 g (0.0181 mol) of methyl (S)-2-(7-chloro-5-methyl-6-oxo-5,6-dihydro-4H-imidazo[1,5-a][1,4]-benzodiazepin-3-yl)-4,5-dihydro-oxazole-4-carboxylate in 700 ml of hot benzene was treated with 2.86 g (0.0199 mol) of copperI bromide and 5.1 ml (0.0272 mol) of tert-butyl perbenzoate according to the method described in Tetr. Letters 1994, 35, 2481. The mixture was boiled at reflux for 20 min., cooled and treated with 300 ml of water. The mixture was filtered, extracted with dichloromethane and chromatographed over silica gel with ethyl acetate as the eluent. There were obtained 3.15 g (47%) of methyl 2-(7-chloro-5-methyl-6-oxo-5,6-dihydro-4H-imidazo[1,5-a][1,4]benzodiazepin-3-yl)-oxazole-4-carboxylate as white crystals; m.p. 266°–268°.

d) 2.90 g (0.00778 mol) of methyl 2-(7-chloro-5-methyl-6-oxo-5,6-dihydro-4H-imidazo[1,5-a][1,4]benzodiazepin-3-yl)-oxazole-4-carboxylate were dissolved in 900 ml of hot tetrahydrofuran and cooled to –78°. The solution was treated dropwise with 29 ml (0.029 mol) of a 1M lithium aluminum hydride solution in tetrahydrofuran and stirred at –78° for 20 hrs. 200 ml of ethyl acetate were added dropwise at –50° and 60 ml of saturated sodium sulphate solution were added dropwise at 0°. The suspension was dried with sodium sulphate, suction filtered and the filtrate was completely freed from the solvents.

The crude product was dissolved in 120 ml of dichloromethane. The solution was treated at room temperature with 2.25 ml (0.031 mol) of thionyl chloride and stirred for 1 hr. The solution was completely freed from the solvents. The residue was partitioned between dichloromethane and saturated sodium bicarbonate solution, extracted, chromatographed over silica gel with ethyl acetate as the eluent and recrystallized from acetonitrile; the mother liquor was then digested with diethyl ether. There were obtained a total of 1.93 g (68%) of 7-chloro-3-(4-chloromethyl-oxazol-2-yl)-5-methyl-5,6-dihydro-4H-imidazo-[1,5-a][1,4]benzodiazepin-6-one as white crystals; m.p. 249°–251°.

e) 0.30 g (0.00082 mol) of 7-chloro-3-(4-chloromethyl-oxazol-2-yl)-5-methyl-5,6-dihydro-4H-imidazo[1,5-a][1,4]-benzodiazepin-6-one was dissolved in 40 ml of tetrahydrofuran, treated with 2.3 ml (0.01 65 mol) of dipropylamine and boiled at reflux for 20 hrs. The solution was completely freed from the solvents, the residue was chromatographed over silica gel with ethyl acetate/ethanol 9:1 as the eluent and recrystallized from ethyl acetate/n-hexane. There was obtained 0.12 g (34%) of 7-chloro-3-(4-dipropylaminomethyl-oxazol-2-yl)-5-methyl-5,6-dihydro-4H-imidazo[1,5-a][1,4]benzodiazepin-6-one as white crystals; m.p. 105°–107°.

f) 0.11 g (0.00026 mol) of 7-chloro-3-(4-dipropylaminomethyl-oxazol-2-yl)-5-methyl-5,6-dihydro-4H-imidazo[1,5-a]-[1,4]benzodiazepin-6-one was dissolved in 10 ml of ethanol and treated with 0.07 ml (0.00026 mol) of 3.7N ethanolic hydrochloric acid. The solution was completely freed from the solvents and recrystallized from ethanol/diethyl ether. There was obtained 0.11 g (91%) of 7-chloro-3-(4-dipropylaminomethyl-oxazol-2-yl)-5-methyl-5,6-dihydro-4H-imidazo[1,5-a][1,4]benzodiazepin-6-one hydrochloride as white crystals; m.p. 218°–220°.

EXAMPLE 30 a) 0.30 g (0.00082 mol) of 7-chloro-3-(4-chloromethyl-oxazol-2-yl)-5-methyl-5,6-dihydro-4H-imidazo[1,5-a][1,4]-benzodiazepin-6-one was dissolved in 40 ml of tetrahydrofuran, treated with 2.3 ml (0.0165 mol) of diisopropylamine and boiled at 150° in an autoclave for 20 hrs. The solution was completely freed from the solvents, the residue was chromatographed over silica gel with ethyl acetate/ethanol 9:1 as the eluent and recrystallized from hot diisopropyl ether. There was obtained 0.11 g (31%) of 7-chloro-3-(4-diisopropylaminomethyl-oxazol-2-yl)-5-methyl-5,6-dihydro-4H-imidazo[1,5-a][1,4]benzodiazepin-6-one as white crystals; m.p. 164°–166°.

b) 0.10 g (0.00023 mol) of 7-chloro-3-(4-diisopropylaminomethyl-oxazol-2-yl)-5-methyl-5,6-dihydro-4H-imidazo[1,5-a][1,4]benzodiazepin-6-one was dissolved in 10 ml of ethanol and treated with 0.063 ml (0.00023 mol) of 3.7N ethanolic hydrochloric acid. The solution was completely freed from the solvents and recrystallized from ethanol/diethyl ether. There was obtained 0.10 g (92%) of 7-chloro-3-(4-diisopropylamino-methyl-oxazol-2-yl)-5-methyl-5,6-dihydro-4H-imidazo[1,5-a][1,4]benzodiazepin-6-one hydrochloride as white crystals; m.p. 228°–230°.

EXAMPLE a) A suspension of 15.5 g (0.0493 mol) of 5-methyl-6-oxo-5,6-dihydro-4H-imidazo[1,5-a]thieno[2,3-f][1,4]diazepine-3-carboxylic acid in 200 ml of dimethylformamide was treated portionwise with 8.07 g (0.0498 mol) of carbonyldiimidazole while gassing with argon. After completion of the CO$_2$ evolution the mixture was stirred at 650 for 1 hr. After cooling to 0°–5° the clear solution obtained was treated with 8.62 g (0.0554 mol) of L-serine methyl ester hydrochloride and with 12.3 ml (0.0554 mol) of triethylamine and stirred at room temperature for 16 hrs. The suspension was completely freed from the solvents. The residue was partitioned between water and ethyl acetate and extracted. The yellow oily residue was chromatographed over silica gel with ethyl acetate as the eluent. There were obtained 17.09 g (95%) of methyl (S)-3-hydroxy-2-(5-methyl-6-oxo-5,6-dihydro-4H-imidazo[1,5-a]thieno[2,3-f][1,4]-diazepin-3-ylcarbonylamino)-propionate as a yellowish oil. An analytical sample was recrystallized from ethyl acetate and gave white crystals; m.p. 158°–160°. $[\alpha]_D^{20}$=+3.9° (CHCl$_3$, c=1%).

b) A solution of 13.7 g (0.0377 mol) of methyl (S)-3-hydroxy-2-(5-methyl-6-oxo-5,6-dihydro-4H-imidazo[1,5-a]thieno[2,3-f][1,4]diazepin-3-ylcarbonylamino)-propionate in 270 ml of tetrahydrofuran was treated while gassing with argon with 9.87 g (0.0414 mol) of methoxycarbonylsulphamoyltriethylammonium hydroxide internal salt (Burgess reagent) according to the method described in Tetr. Letters 1992, 33, 907. The mixture was boiled at reflux for 2 hrs. and completely freed from the solvents. The residue was partitioned between water and dichloromethane, extracted, chromatographed over silica gel with ethyl acetate as the eluent and recrystallized from acetonitrile. There were obtained 2.94 g (22%) of methyl (S)-2-(5-methyl-6-oxo-5,6-dihydro-4H-imidazo[1,5-a]thieno[2,3-f][1,4]diazepin-3-yl)-4,5-dihydro-oxazole-4-carboxylate as white crystals; m.p. 215°–217°. $[\alpha]_D^{20}$=+41.2° (CHCl$_3$, c=1%). A further 3.25 g (25%) of yellowish crystals were recovered from the mother liquor.

c) A solution of 5.92 g (0.0171 mol) of methyl (S)-2-(5-methyl-6-oxo-5,6-dihydro-4H-imidazo[1,5-a]thieno[2,3-f][1,4]-diazepin-3-yl)-4,5-dihydro-oxazole-4-carboxylate in 300 ml of benzene was treated with 2.69 g (0.0188 mol) of copper$^I$ bromide and 4.97 ml (0.0256 mol) of tert-butyl perbenzoate according to the method described in Tetr. Letters 1994, 35, 2481. The mixture was boiled at reflux for 1 hr., cooled and treated with 100 ml of water. The mixture was filtered, extracted with benzene and chromatographed over silica gel with ethyl acetate as the eluent. There were obtained 1.48 g (25%) of methyl 2-(5-methyl-6-oxo-5,6-dihydro-4H-imidazo[1,5-a]thieno[2,3-f][1,4]-diazepin-3-yl)-oxazole-4-carboxylate as a yellowish solid. An analytical sample was recrystallized from hot ethyl acetate and gave white crystals; m.p. 254°–255°.

d) 0.705 g (0.00205 mol) of methyl 2-(5-methyl-6-oxo-5,6-dihydro-4H-imidazo[1,5-a]thieno[2,3-f][1,4]diazepin-3-yl)-oxazole-4-carboxylate was dissolved in 350 ml of hot tetrahydrofuran and cooled to –78°. The solution was treated dropwise with 6.14 ml (0.00614 mol) of a 1M lithium aluminum hydride solution in tetrahydrofuran and stirred at –78° for 20 hrs. 100 ml of ethyl acetate were added dropwise at –50° and 6 ml of saturated sodium sulphate solution were added dropwise at 0°. The suspension was dried with sodium sulphate, suction filtered and the filtrate was completely freed from the solvents.

The crude product was dissolved in 70 ml of dichloromethane. The solution was treated at room temperature with 0.59 ml (0.00818 mol) of thionyl chloride and stirred for 1 hr. The solution was treated with saturated sodium bicarbonate solution, extracted, chromatographed over silica gel with ethyl acetate as the eluent and recrystallized from hot acetonitrile. There were obtained 0.217 g (32%) of 3-(4-chloromethyl-oxazol-2-yl)-5-methyl-5,6-dihydro-4H-imidazo[1,5-a]thieno[2,3-f][1,4]-diazepin-6-one as white crystals; m.p. 200°–206°.

e) 0.167 g (0.000498 mol) of 3-(4-chloromethyl-oxazol-2-yl)-5-methyl-5,6-dihydro-4H-imidazo[1,5-a]thieno[2,3-f][1,4]-diazepin-6-one was dissolved in 20 ml of tetrahydrofuran, treated with 1.4 ml (0.0102 mol) of dipropylamine and boiled at reflux for 20 hrs. The solution was completely freed from the solvents, the residue was chromatographed over silica gel with ethyl acetate/ethanol 1:1 as the eluent and recrystallized from diisopropyl ether. There was obtained 0.075 g (38%) of 3-(4-dipropylaminomethyl-oxazol-2-yl)-5-methyl-5,6-dihydro-4H-imidazo[1,5-a]thieno[2,3-f][1,4]diazepin-6-one as white crystals; m.p. 110°–111°.

f) 0.075 g (0.00019 mol) of 3-(4-dipropylaminomethyl-oxazol-2-yl)-5-methyl-5,6-dihydro-4H-imidazo[1,5-a]thieno-[2,3-f][1,4]diazepin-6-one was dissolved in 50 ml of ethanol and treated with 0.05 ml (0.00019 mol) of 3.7N ethanolic hydrochloric acid. The solution was completely freed from the solvents and recrystallized from ethanol/diethyl ether. There was obtained 0.07 g (86%) of 3-(4-dipropylaminomethyl-oxazol-2-yl)-5-methyl-5,6-dihydro-4H-imidazo[1,5-a]thieno[2,3-f][1,4]-diazepin-6-one hydrochloride as whitish yellow crystals; m.p. 210°–215°.

EXAMPLE A 3-(5-Dipropylaminomethyl-oxazol-2-yl)-8-fluoro-5-methyl-5,6-dihydro-4H-imidazo[1,5-a)[1,4]benzodiazepin-6-one can be used as the active ingredient for the production of an injection solution of the following composition:

| | |
|---|---|
| Active ingredient | 1 mg |
| 1N HCl | 20 µl |
| Acetic acid | 0.5 mg |
| NaCl | 8 mg |
| Benzyl alcohol | 10 mg |
| 1N NaOH | q.s. ad pH 5 |
| H$_2$O | q.s. ad 1 ml |

We claim:
1. Imidazodiazepinones of the formula

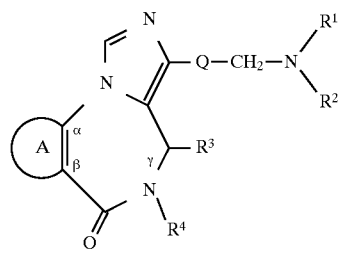

I wherein A and the two carbon atoms denoted by α and β together signify

(A$^1$)

;

Q signifies one of the residues

(Q$^1$)

(Q$^2$)

and 

(Q$^3$)

;

R$^1$ and R$^2$ each signify hydrogen, lower alkyl, lower alkenyl, lower alkynyl, lower hydroxyalkyl, lower alkoxy-lower alkyl, (C$_3$–C$_6$)-cycloalkyl, (C$_3$–C$_6$)-cycloalkyl-lower alkyl, amino-lower alkyl, lower alkylamino-lower alkyl, di-lower alkylamino-lower alkyl or aryl-lower alkyl or together with the nitrogen atom signify a 5- to 8-membered heterocycle optionally containing a further hetero atom or a fused benzene ring, R$^3$ signifies hydrogen and R$^4$ signifies lower alkyl or R$^3$ and R$^4$ together signify a di- or trimethylene group and R⁵ and R⁶ each signify hydrogen, halogen, trifluoromethyl, lower alkoxy or nitro, with the carbon atom denoted by γ having the S-configuration when R³ is different from hydrogen, and pharmaceutically acceptable acid addition salts thereof.

2. Compounds according to claim 1, wherein Q signifies Q¹ or Q² and all other substituents correspond to the significance in claim 1.

3. Compounds according to claim 2, wherein Q signifies the residue Q¹, R¹ and R² each signify lower alkyl, A signifies a residue of formula A¹ in which R⁵ and R⁶ each signify hydrogen or halogen.

4. 3-(5-Dipropylaminomethyl-oxazol-2-yl)-8-fluoro-5-methyl-5,6-dihydro-4H-imidazo[1,5-a][1,4]benzodiazepin-6-one.

5. A pharmaceutical composition comprising an effective amount for sedating a host of a compound of the formula

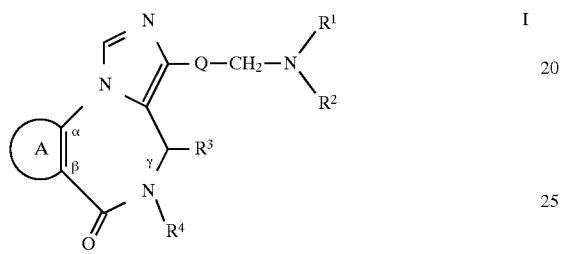

wherein A and the two carbon atoms denoted by α and β together signify

Q signifies one of the residues

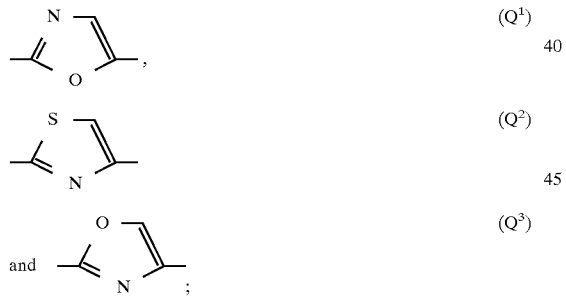

R¹ and R² each signify hydrogen, lower alkyl, lower alkenyl, lower alkynyl, lower hydroxyalkyl, lower alkoxy-lower alkyl, (C₃–C₆)-cycloalkyl, (C₃–C₆)-cycloalkyl-lower alkyl, amino-lower alkyl, lower alkylamino-lower alkyl, di-lower alkylamino-lower alkyl or aryl-lower alkyl or together with the nitrogen atom signify a 5- to 8-membered heterocycle optionally containing a further hetero atom or a fused benzene ring, R³ signifies hydrogen and R⁴ signifies lower alkyl or R³ and R⁴ together signify a di- or trimethylene group and R⁵ and R⁶ each signify hydrogen, halogen, trifluoromethyl, lower alkoxy or nitro, with the carbon atom denoted by γ having the S-configuration when R³ is different from hydrogen, and pharmaceutically acceptable acid addition salts thereof and a therapeutically inert carrier.

6. (S)-8-Chloro-1-(5-dipropylaminomethyl-oxazol-2-yl)-12,12a-dihydro-9H,11 H-azeto[2,1-c]imidazo[1,5-a][1,4]-benzodiazepin-9-one.

7. A method of sedating a host comprising administering an effective amount of a compound of the formula

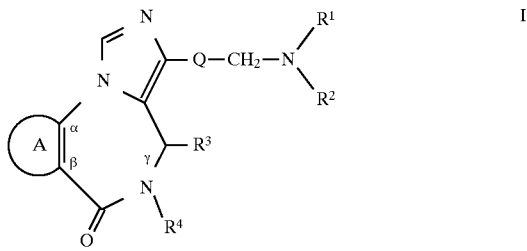

wherein A and the two carbon atoms denoted by α and β together signify

Q signifies one of the residues

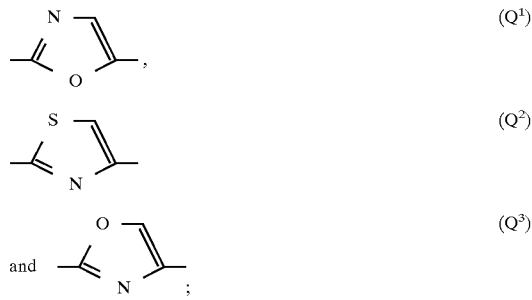

R¹ and R² each signify hydrogen, lower alkyl, lower alkenyl, lower alkynyl, lower hydroxyalkyl, lower alkoxy-lower alkyl, (C₃–C₆)-cycloalkyl, (C₃–C₆)-cycloalkyl-lower alkyl, amino-lower alkyl, lower alkylamino-lower alkyl, di-lower alkylamino-lower alkyl or aryl-lower alkyl or together with the nitrogen atom signify a 5- to 8-membered heterocycle optionally containing a further hetero atom or a fused benzene ring, R³ signifies hydrogen and R⁴ signifies lower alkyl or R³ and R⁴ together signify a di- or trimethylene group and R⁵ and R⁶ each signify hydrogen, halogen, trifluoromethyl, lower alkoxy or nitro, with the carbon atom denoted by γ having the S-configuration when R³ is different from hydrogen, and pharmaceutically acceptable acid addition salts thereof.

8. Compounds according to claim 2, wherein Q signifies the residue Q², R¹ and R² each signify lower alkyl, A signifies a residue of formula A¹, R³ signifies hydrogen and R⁴ signifies methyl or R³ and R⁴ together signify a di- or trimethylene group.

9. 7-Chloro-3-(4-dipropylaminomethyl-thiazol-2-yl)-5-methyl-5,6-dihydro-4H-imidazo[1,5-a][1,4]benzodiazepin-6-one.

10. (S)-8-Chloro-1-(4-dipropylaminomethyl-thiazol-2-yl)-2,12a-dihydro-9H,11H-azeto[2,1-c]amidazo[1,5-a][1,4]-benzodiazepin-9-one.

11. (S)-8-Chloro-1-(4-dipropylaminomethyl-thiazol-2-yl)-11,12,13,13a-tetrahydro-9H-imidazo[1,5-a]pyrrolo[2,1-c][1,4]benzodiazepin-9-one and 7-chloro-3-(4-dipropylaminomethyl-thiazol-2-yl)-8-fluoro-5-methyl-5,6-dihydro-4H-imidazo[1,5-a][1,4]benzodiazepin-6-one.

12. Compounds according to claim 1, wherein Q signifies the residue $Q^3$, $R^1$ and $R^2$ each signify lower alkyl, A signifies a residue of formula $A^1$, $R^3$ signifies hydrogen and $R^4$ signifies methyl.

13. 7-Chloro-3-(4-dipropylamino-methyl-oxazol-2-yl)-5-methyl-5,6-dihydro-4H-imidazo[1,5-a][1,4]benzodiazepin-6-one.

14. A method of treating or preventing convulsions comprising administering an effective amount of a compound of the formula

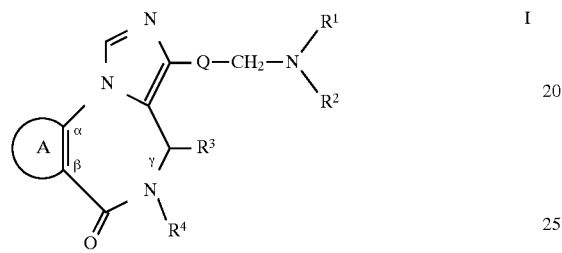
(I)

wherein A and the two carbon atoms denoted by α and β together signify

($A^1$)

Q signifies one of the residues

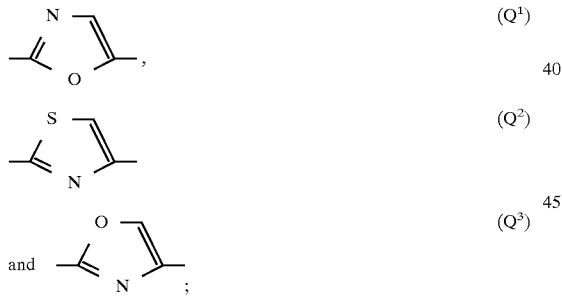
($Q^1$)
($Q^2$)
($Q^3$)

$R^1$ and $R^2$ each signify hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl or together with the nitrogen atom signify a 5- to 8-membered heterocycle optionally containing a further hetero atom or a fused benzene ring, $R^3$ signifies hydrogen and $R^4$ signifies lower alkyl or $R^3$ and $R^4$ together signify a di- or trimethylene group and $R^5$ and $R^6$ each signify hydrogen, halogen, trifluoromethyl, lower alkoxy or nitro, with the carbon atom denoted by γ having the S-configuration when $R^3$ is different from hydrogen, and pharmaceutically acceptable acid addition salts thereof.

15. A process for the manufacture of compounds according to claim 1, which process comprises a) reacting a compound of the general formula

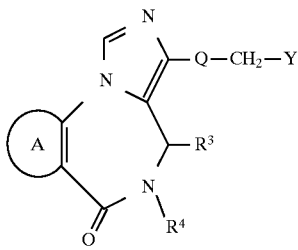
(II)

wherein A, Q, $R^3$ and $R^4$ have the above significance and Y signifies a leaving group, with an amine of the general formula

(III)

wherein $R^1$ and $R^2$ have the above significance, or b) cleaving off the protecting group(s) from a compound of the general formula

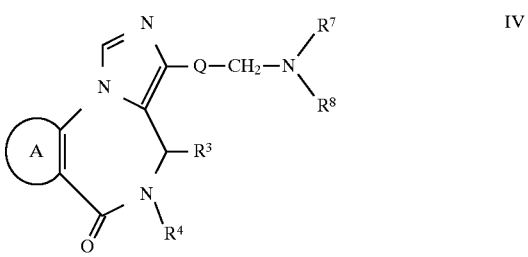
(IV)

wherein A, Q, $R^3$ and $R^4$ have the above significance and $R^7$ signifies a protecting group, protected lower hydroxyalkyl, protected amino-lower alkyl or protected lower alkyl-amino-lower alkyl and $R^8$ signifies hydrogen, lower alkyl, lower alkenyl, lower alkynyl, protected lower hydroxyalkyl, lower alkoxy-lower alkyl, ($C_3$–$C_6$)-cycloalkyl, ($C_3$–$C_6$)-cycloalkyl-lower alkyl, protected amino-lower alkyl, protected lower alkylamino-lower alkyl, di-lower alkyl-amino-lower alkyl, or aryl-lower alkyl or $R^7$ and $R^8$ together signify a protecting group, or c) N-alkylating a compound of the general formula

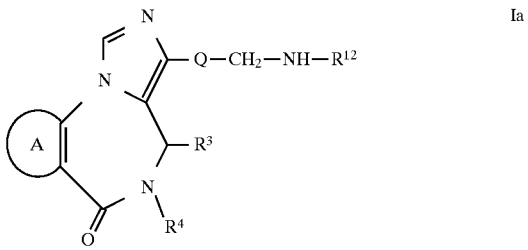
(Ia)

wherein A, Q, $R^3$ and $R^4$ have the above significance and $R^{12}$ signifies hydrogen, lower alkyl, lower alkenyl, lower alkynyl, lower hydroxyalkyl, lower alkoxy-lower alkyl, ($C_3$–$C_6$)-cycloalkyl, ($C_3$–$C_6$)-cycloalkyl-lower alkyl, amino-lower alkyl, lower alkylamino-lower alkyl, di-lower alkylamino-lower alkyl or aryl-lower alkyl, or d) reducing a compound of the general formula

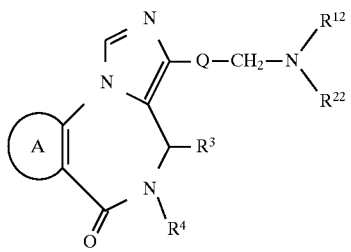
Ib wherein A, Q R$^3$ and R$^4$ and R$^{12}$ have the above significance and R$^{22}$ signifies lower alkenyl or lower alkynyl, and, if desired, e) converting a compound of general formula I into a pharmaceutically usable acid addition salt.

16. 7-Chloro-3-(5-dipropylaminomethyl-oxazol-2-yl)-8-fluoro-5-methyl-5,6-dihydro-4H-imidazo[1,5-a][1,4]benzodiazepin-6-one, 3-(5-dipropylaminomethyl-oxazol-2-yl)-5-methyl-5,6-dihydro-4H-imidazo[1,5-a][1,4]benzodiazepin-6-one;

7-chloro-3-(5-dipropylaminomethyl-oxazol-2-yl)-5-methyl-5,6-dihydro-4H-imidazo[1,5-a][1,4]benzodiazepin-6-one; and 3-(5-dipropylamiomethyl-oxazol-2-yl)-8-fluoro-5-methyl-5,6-dihydro-4H-imidazo[1,5-a][1,4]benzodiazepin-6-one.

* * * * *